(12) United States Patent
Hebeisen et al.

(10) Patent No.: US 7,629,346 B2
(45) Date of Patent: Dec. 8, 2009

(54) PYRAZINECARBOXAMIDE DERIVATIVES AS CB1 ANTAGONISTS

(75) Inventors: Paul Hebeisen, Basel (CH); Hans Iding, Rheinfelden (DE); Matthias Heinrich Nettekoven, Grenzach-Wyhlen (DE); Ulrike Obst Sander, Reinach (CH); Stephan Roever, Inzlingen (DE); Urs Weiss, Pratteln (CH); Beat Wirz, Reinach (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/809,047

(22) Filed: May 30, 2007

(65) Prior Publication Data
US 2007/0293509 A1 Dec. 20, 2007

(30) Foreign Application Priority Data
Jun. 19, 2006 (EP) .................... 06115646

(51) Int. Cl.
*A61K 31/4965* (2006.01)
*A61K 31/497* (2006.01)
(52) U.S. Cl. .................... 514/255.05; 514/255.06; 544/405; 544/406; 544/407; 544/315; 546/268.1
(58) Field of Classification Search .................. 544/406
See application file for complete search history.

(56) References Cited

U.S. PATENT DOCUMENTS

| | | | |
|---|---|---|---|
| 3,940,418 A | 2/1976 | Hamilton | |
| 5,462,960 A | 10/1995 | Barth et al. | |
| 5,596,106 A | 1/1997 | Cullinan et al. | |
| 5,624,941 A | 4/1997 | Barth et al. | |
| 6,028,084 A | 2/2000 | Barth et al. | |
| 6,355,631 B1 | 3/2002 | Achard et al. | |
| 6,432,984 B1 | 8/2002 | Barth et al. | |
| 6,479,479 B2 | 11/2002 | Achard et al. | |
| 6,509,367 B1 | 1/2003 | Martin et al. | |
| 6,566,356 B2 | 5/2003 | Achard et al. | |
| 6,645,985 B2 | 11/2003 | Barth et al. | |
| 6,734,176 B2 | 5/2004 | Achard et al. | |
| 6,872,717 B2 | 3/2005 | Achard et al. | |
| 6,893,659 B2 | 5/2005 | Abramovici et al. | |
| 6,906,080 B1 | 6/2005 | Barth et al. | |
| 7,037,944 B2 | 5/2006 | Piot-Grosjean et al. | |
| 7,132,414 B2 | 11/2006 | Achard et al. | |
| 7,148,258 B2 | 12/2006 | Piot-Grosjean et al. | |
| 7,229,999 B2 * | 6/2007 | Hebeisen et al. ............ 514/256 |
| 2001/0027193 A1 | 10/2001 | Achard et al. | |
| 2002/0019383 A1 | 2/2002 | Achard et al. | |
| 2002/0091114 A1 | 7/2002 | Piot-Grosjean et al. | |
| 2002/0188007 A1 | 12/2002 | Barth et al. | |
| 2003/0003145 A1 | 1/2003 | Abramovici et al. | |
| 2003/0055033 A1 | 3/2003 | Achard et al. | |
| 2003/0119810 A1 | 6/2003 | Achard et al. | |
| 2004/0039024 A1 | 2/2004 | Barth et al. | |
| 2004/0157823 A1 | 8/2004 | Achard et al. | |
| 2004/0192667 A1 | 9/2004 | Makriyannis et al. | |
| 2004/0259887 A1 | 12/2004 | Dow | |
| 2005/0032773 A1 | 2/2005 | Piot-Grosjean et al. | |
| 2005/0032774 A1 | 2/2005 | Piot-Grosjean et al. | |
| 2005/0130953 A1 | 6/2005 | Achard et al. | |
| 2005/0192332 A1 | 9/2005 | Barth et al. | |
| 2006/0189664 A1 | 8/2006 | Barth et al. | |
| 2006/0258709 A1 | 11/2006 | Piot-Grosjean et al. | |
| 2008/0070931 A1 | 3/2008 | Hebeisen et al. | |
| 2008/0085905 A1 | 4/2008 | Dietz et al. | |

FOREIGN PATENT DOCUMENTS

| | | |
|---|---|---|
| EP | 576357 | 12/1993 |
| EP | 656354 | 6/1995 |
| EP | 658546 | 6/1995 |
| FR | 2856684 | 12/2004 |
| WO | WO 96/02248 | 2/1996 |
| WO | WO 97/19063 | 5/1997 |
| WO | WO 98/31227 | 7/1998 |
| WO | WO 98/41519 | 9/1998 |
| WO | WO 98/43635 | 10/1998 |
| WO | WO 98/43636 | 10/1998 |
| WO | WO 00/15609 | 3/2000 |
| WO | WO 00/46209 | 8/2000 |

(Continued)

OTHER PUBLICATIONS

Pacheco et al., J. Pharmacol. Exp. Ther., 257(1), pp. 170-183 (1991).

(Continued)

*Primary Examiner*—James O Wilson
*Assistant Examiner*—Brian McDowell
(74) *Attorney, Agent, or Firm*—George W. Johnston; Dennis P. Tramaloni; Brian C. Remy

(57) ABSTRACT

The present invention relates to compounds of the formula I:

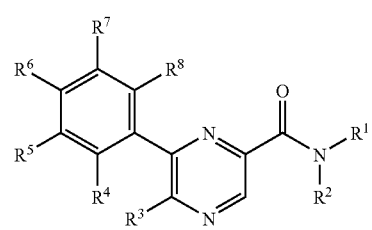

wherein $R^1$ to $R^8$ are as defined in the description and claims, and pharmaceutically acceptable salts thereof. The compounds are useful for the treatment and/or prophylaxis of diseases which are associated with the modulation of CB1 receptors, such as obesity.

22 Claims, No Drawings

FOREIGN PATENT DOCUMENTS

| | | |
|---|---|---|
| WO | WO 01/32663 | 5/2001 |
| WO | WO 01/64632 | 9/2001 |
| WO | WO 01/64633 | 9/2001 |
| WO | WO 01/64634 | 9/2001 |
| WO | WO 01/70700 | 9/2001 |
| WO | WO 02/28346 | 4/2002 |
| WO | WO 03/051850 | 6/2003 |
| WO | WO 03/051851 | 6/2003 |
| WO | WO 03/084930 | 10/2003 |
| WO | WO 2004/0099157 | 11/2004 |
| WO | WO 2004/110453 | 12/2004 |
| WO | WO 2004/111033 | 12/2004 |
| WO | WO 2004/111033 A1 | 12/2004 |
| WO | WO 2004/111034 | 12/2004 |
| WO | WO 2004/111039 | 12/2004 |
| WO | WO 2004111038 | 12/2004 |
| WO | WO 2006/106054 A1 | 10/2006 |
| WO | WO 2007/011760 A2 | 1/2007 |

OTHER PUBLICATIONS

Casiano et al., NIDA Res. Monogr., 105, pp. 295-296 (1991).
Hosohata et al., Life Sci., 61, pp. 115-118 (1997).
Pertwee et al., Life Sci., 56(23-24), pp. 1949-1955 (1995).
Felder et al., J. Pharmacol. Exp. Ther., 284(1), pp. 291-297 (1998).
Kanyonyo et al., Bioorg. Med. Chem. Lett. 9(15), pp. 2233-2236 (1999).
Ooms et al., J. Med. Chem., 45(9), pp. 1748-1756 (2002).
Barth et al., "*Cannabinoid Antagonists; From Research Tools to Potential New Drugs*", Abstracts of Papers, 222$^{nd}$ ACS National Meeting, Chicago, IL, USA, Aug. 26-30, 2001.
Database Beilstein, XP002457050 & Agric. Biol. Chem., vol. 48, No. 4, pp. 1009-1016 (1984).

* cited by examiner

PYRAZINECARBOXAMIDE DERIVATIVES AS CB1 ANTAGONISTS

PRIORITY TO RELATED APPLICATION(S)

This application claims the benefit of European Patent Application No. 06115646.9, filed Jun. 19, 2006, which is hereby incorporated by reference in its entirety.

BACKGROUND OF THE INVENTION

The present invention relates to novel 2-pyrazinecarboxamide derivatives, their manufacture, pharmaceutical compositions containing them and their use as medicaments. The active compounds of the present invention are modulators of the $CB_1$ receptor (a cannabinoid receptor) and are useful in treating obesity and other disorders.

Two different subtypes of cannabinoid receptors ($CB_1$ and $CB_2$) have been isolated and both belong to the G protein coupled receptor superfamily. Alternative spliced forms of $CB_1$, $CB_{1A}$ and $CB_{1B}$ have also been described, but are expressed only at low levels in the tissues tested. (D. Shire, C. Carrillon, M. Kaghad, B. Calandra, M. Rinaldi-Carmona, G. Le Fur, D. Caput, P. Ferrara, J. Biol. Chem. 270 (8) (1995) 3726-31; E. Ryberg, H. K. Vu, N. Larsson, T. Groblewski, S. Hjorth, T. Elebring, S. Sjögren, P. J. Greasley, FEBS Lett. 579 (2005) 259-264). The $CB_1$ receptor is mainly located in the brain and to a lesser extent in several peripheral organs, whereas the $CB_2$ receptor is predominately distributed in the periphery primarily localized in spleen and cells of the immune system (S. Munro, K. L. Thomas, M. Abu-Shaar, Nature 365 (1993) 61-61). Therefore in order to avoid side effects a $CB_1$-selective compound is desirable.

$\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *cannabis sativa* (marijuanan), and has medicinal uses (R. Mechoulam (Ed.) in "*Cannabinoids as therapeutic Agents*", 1986, pp. 1-20, CRC Press). $\Delta^9$-THC is a non-selective $CB_1/_2$ receptor agonist and is available in the USA as dronabinol (marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539-545, E. M. Williamson, F. J. Evans, Drugs 60 (6) (2000) 1303-1314).

Anandamide (arachidonylethanolamide) was identified as the endogenous ligand (agonist) for $CB_1$ (R. G. Pertwee, Curr. Med. Chem., 6 (8) (1999) 635-664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946-9). Anandamide and 2-arachidonoylglycerol (2-AG) modulate at the presynaptic nerve terminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521-8), thereby affecting neurotransmitter release and/or action, which decreases the release of neurotransmitter (A. C. Porter, C. C. Felder, Pharmacol. Ther., 90 (1) (2001) 45-60).

Anandamide as $\Delta^9$-THC also increases feeding through $CB_1$ receptor-mediated mechanism. $CB_1$ selective antagonists block the increase in feeding associated with administration of anandamide (C. M. Williams, T. C. Kirkham, Psychopharmacology 143 (3) (1999) 315-317; C. C. Felder, E. M. Briley, J. Axelrod, J. T. Simpson, K. Mackie, W. A. Devane, Proc. Natl. Acad. Sci. U.S.A. 90 (16) (1993) 7656-60) and cause appetite suppression and weight loss (G. Colombo, R. Agabio, G. Diaz, C. Lobina, R. Reali, G. L. Gessa, Life Sci. 63 (8) (1998) L113-PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822-825).

At least two CB1 selective antagonist/inverse agonists (SR-141716 and SLV-319) are currently undergoing clinical trials for the treatment of obesity and/or smoking cessation. In a double blind placebo-controlled study, at the doses of 10 and 20 mg daily, SR 141716 significantly reduced body weight when compared to placebo (F. Barth, M. Rinaldi-Carmona, M. Arnone, H. Heshmati, G. Le Fur, "*Cannabinoid antagonists: From research tools to potential new drugs*." Abstracts of Papers, 222nd ACS National Meeting, Chicago, Ill., United States, Aug. 26-30, 2001). SR-141716 reduced body weight, waist circumference and improved metabolic parameters (plasma HDL, triglycerides and insulin sensitivity) in several phase III studies (RIO-lipids, RIO-Europe and RIO-North America). Additionally SR-141716 has shown efficacy in a phase III trial for smoking cessation (STRATUS-US).

Substituted pyridines, pyrimidines and pyrazines having activity against the cannabinoid receptors are for example disclosed in US patent application US 04/0259887 and in PCT patent applications WO 03/051850, WO 03/051851, WO 03/084930, WO 04/110453, WO 04/111033, WO 04/111034, WO 04/111038, WO 04/111039 and in patent application FR 2856684.

Other compounds which have been proposed as CB1 receptor antagonists respectively inverse agonists are substituted pyrazoles as disclosed in U.S. Pat. Nos. 5,624,941, 6,028,084 and 6,509,367, in PCT patent applications WO 98/031227, WO 98/041519, WO 98/043636, WO 98/043635, WO 04/192667, WO 04/0099157 and in patent application EP 658546 or aminoalkylindols (AAI; M. Pacheco, S. R. Childers, R. Arnold, F. Casiano, S. J. Ward, J. Pharmacol. Exp. Ther. 257 (1) (1991) 170-183). Examples of aminoalkylindoles are 6-bromo-(WIN54661; F. M. Casiano, R. Arnold, D. Haycock, J. Kuster, S. J. Ward, NIDA Res. Monogr. 105 (1991) 295-6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115-118; R. Pertwee, G. Griffin, S. Fernando, X. Li, A. Hill, A. Makriyannis, Life Sci. 56 (23-24) (1995) 1949-55). Furthermore, arylbenzo[b]thiophene and benzo[b]furan derivatives (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291-7) as disclosed in WO 96/02248 or U.S. Pat. No. 5,596,106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233-2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748-1756) are known to antagonize the $CB_1$ receptor respectively act as an inverse agonist on the $hCB_1$ receptor. In WO 00/15609 (FR2783246-A1), WO 01/64634 (FR2805817-A1), WO 02/28346, WO 01/64632 (FR2805818-A1) and WO 01/64633 (FR2805810-A1) are disclosed substituted 1-bis(aryl)methyl-azetidines derivatives as antagonists of $CB_1$. In WO 01/70700 4,5-dihydro-1H-pyrazole derivatives are described as $CB_1$ antagonists. In several patent documents bridged and non-bridged 1,5-diphenyl-3-pyrazolecarboxamide derivatives are disclosed as $CB_1$ antagonists/inverse agonists (WO 01/32663, WO 00/46209, WO 97/19063, EP 658546, EP 656354, U.S. Pat. No. 5,624,941, EP 576357 and U.S. Pat. No. 3,940,418). However, there still remains a need for potent low molecular weight CB1 modulators that have improved pharmacokinetic and pharmacodynamic properties suitable for use as human pharmaceuticals.

It is therefore an object of this invention to provide selective, directly acting CB1 receptor antagonists/inverse agonists. Such antagonists/inverse antagonists are useful in medical therapy, particularly in the treatment and/or prevention of diseases which are associated with the modulation of CB1 receptors.

SUMMARY OF THE INVENTION

The present invention relates to the compounds of the formula (I) including all pharmaceutically acceptable salts thereof wherein formula (I) is:

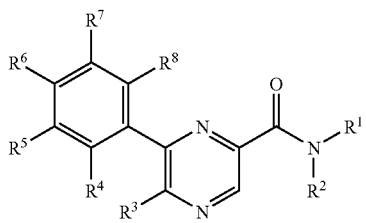

I wherein $R^1$-$R^8$ are as defined in the detailed description and in the claims. The compounds of the present invention are modulators of the $CB_1$ receptor and are useful in the treatment and/or prophylaxis of eating disorders, obesity, type II diabetes, and substance abuse and/or addiction (including alcohol dependency and nicotine dependency). In addition, the invention is concerned with a process for the manufacture of the above compounds, pharmaceutical compositions which contain such compounds as well as methods of using such compounds.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven carbon atoms. In preferred embodiments such "lower" groups will have one to four carbon atoms.

The term "alkyl", alone or in combination with other groups, refers to a branched or straight-chain monovalent saturated aliphatic hydrocarbon radical of one to twenty carbon atoms. In certain preferred embodiments, the alkyl is one to sixteen carbon atoms, and more preferably one to ten carbon atoms.

The term "lower alkyl" or "$C_{1-7}$-alkyl," alone or in combination with other groups, refers to a branched or straight-chain monovalent alkyl radical of one to seven carbon atoms. In preferred embodiments, the lower alkyl has one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" or "$C_{1-7}$-alkoxy" refers to the group R'—O—, wherein R' is lower alkyl. Examples of lower alkoxy groups include methoxy, ethoxy, propoxy, isopropoxy, butoxy, isobutoxy and hexyloxy, with methoxy being especially preferred.

The term "lower alkoxyalkyl" or "$C_{1-7}$-alkoxy-$C_{1-7}$-alkyl" refers to a lower alkyl group as defined previously which is mono-substituted or multiply substituted with a lower alkoxy group as defined above. Examples of lower alkoxyalkyl groups include —$CH_2$—O—$CH_3$, —$CH_2$—$CH_2$—O—$CH_3$, —$CH_2$—O—$CH_2$—$CH_3$ and the groups specifically exemplified herein. Most preferably, the lower alkoxyalkyl is methoxyethyl.

The term "lower hydroxyalkyl" or "hydroxy-$C_{1-7}$-alkyl" refers to lower alkyl groups as defined previously wherein at least one of the hydrogen atoms of the lower alkyl group is replaced by a hydroxy group. Examples of lower hydroxyalkyl groups include hydroxymethyl, 2-hydroxybutyl, 3-hydroxy-2,2-dimethylpropyl and the groups specifically exemplified therein.

The term "halogen" refers to fluorine, chlorine, bromine or iodine. Preferred "halogen" groups are fluorine or chlorine.

The term "lower halogenalkyl" or "halogen-$C_{1-7}$-alkyl" refers to lower alkyl groups which are mono-substituted or multiply substituted with halogen. In preferred embodiments, the halogen substituent is fluoro or chloro, most preferably fluoro. Examples of lower halogenalkyl groups include —$CF_3$, —$CHF_2$, —$CH_2Cl$, —$CH_2CF_3$, —$CH(CF_3)_2$, —$CF_2$—$CF_3$ and the groups specifically exemplified herein.

The term "lower halogenalkoxy" or "halogen-$C_{1-7}$-alkoxy" refers to lower alkoxy groups as defined previously wherein at least one of the hydrogen atoms of the lower alkoxy group is replaced by a halogen atom. In preferred embodiments, the halogen substituent is fluoro or chloro, most preferably fluoro. Included among the preferred halogenated lower alkyl groups are trifluoromethoxy, difluoromethoxy, fluoromethoxy and chloromethoxy, with trifluoromethoxy being especially preferred.

The term "cycloalkyl" or "$C_{3-7}$-cycloalkyl" refers to a monovalent carbocyclic radical of three to seven carbon atoms. In preferred embodiments, the cycloalkyl or $C_{3-7}$-cycloalkyl has three to five carbon atoms. Examples of cycloalkyls include cyclopropyl, cyclobutyl, cyclopentyl, cyclohexyl and cycloheptyl, with cyclopropyl being especially preferred.

The term "lower cycloalkylalkyl" or "$C_{3-7}$-cycloalkyl-$C_{1-7}$-alkyl" refers to a lower alkyl group as defined previously which is mono-substituted or multiply substituted with a cycloalkyl group as defined previously. Examples of lower cycloalkylalkyl groups include —$CH_2$-cyclopropyl, —$CH_2$—$CH_2$-cyclopropyl, —$CH_2$-cyclopentyl and the groups specifically exemplified herein.

The term "heterocyclyl" refers to a saturated or partly unsaturated 3-, 4-, 5-, 6- or 7-membered ring containing one, two or three heteroatoms independently selected from the group consisting of nitrogen, oxygen and sulphur. Examples of heterocyclyls include piperidinyl, piperazinyl, azetidinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, oxiranyl, thiadiazolylidinyl, oxetanyl, dioxolanyl, dihydrofuryl, tetrahydrofuryl, dihydropyranyl, tetrahydropyranyl, and thiomorpholinyl. Preferred heterocyclyls are oxetanyl, tetrahydrofuryl and [1,3]dioxolanyl, with tetrahydrofruyl being especially preferred.

The term "lower heterocyclylalkyl" or "heterocyclyl-$C_{1-8}$-alkyl" refers to lower alkyl groups as defined previously wherein at least one of the hydrogen atoms of the lower alkyl group is replaced by a heterocyclyl group as defined previously.

The term "heteroaryl" refers to an aromatic 5- or 6-membered ring containing one, two or three heteroatoms independently selected from the group consisting of nitrogen, oxygen and sulphur. The term "heteroaryl" also refers to bicyclic aromatic moieties having 9 to 10 ring atoms containing 1 to 3 heteroatoms independently selected from the group consisting of nitrogen, oxygen and sulphur. The heteroaryl group can optionally be mono-substituted or disubstituted by lower alkyl. Examples of heteroaryl groups include furyl, pyridyl, pyrazinyl, pyrimidinyl, pyridazinyl, thienyl, isoxazinyl, thiazolyl, isothiazolyl, oxazolyl, imidazolyl, pyrazolyl, triazolyl, oxadiazolyl, oxatriazolyl, tetrazolyl, pentazolyl, and pyrrolyl. Examples of heteroaryls that are bicyclic aromatic moieties as defined above include benzofuranyl, benzothiazolyl, indolyl, benzoxazolyl, quinolinyl, isoquinolinyl, benzimidazolyl, benzisoxazolyl, and benzothienyl. Preferred heteroaryl groups are isoxazolyl, pyridyl, pyrazinyl, pyrimidinyl, pyridazinyl, imidazolyl, triazolyl, and thiazolyl which groups can optionally be mono-substituted or disubstituted by lower alkyl. Especially preferred are pyridyl, pyrazinyl, pyridazinyl and pyrimidinyl.

The term "lower heteroarylalkyl" or "heteroaryl-$C_{1-8}$-alkyl" refers to lower alkyl groups as defined previously wherein at least one of the hydrogen atoms of the lower alkyl group is replaced by a heteroaryl group as defined previously.

The term "a therapeutically effective amount" of a compound refers to an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 10,000 mg, and preferably from about 1 mg to about 1,000 mg should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The term "pharmaceutically acceptable salts" encompasses salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In detail, the present invention relates to the compounds of formula I and all pharmaceutically acceptable salts thereof wherein formula I is:

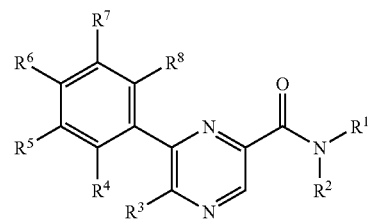

I wherein:
(a) $R^1$ is selected from the group consisting of:
  (1) cycloalkyl, which is optionally substituted by a substituent selected from the group consisting of hydroxy, lower alkoxy and lower hydroxyalkyl,
  (2) —$CH_2$—$(CR^9R^{10})_m$-cycloalkyl, wherein:
    (A) $R^9$ is selected from the group consisting of hydrogen, lower alkyl and cycloalkyl;
    (B) $R^{10}$ is selected from the group consisting of hydrogen, hydroxy and lower alkoxy;
    (C) m is 0 or 1, and
    (D) the cycloalkyl is optionally substituted by hydroxy or lower hydroxyalkyl,
  (3) piperidinyl, and
  (4) —$CR^{11}R^{12}$—$COOR^{13}$; wherein:
    (A) $R^{11}$ is hydrogen or lower alkyl,
    (B) $R^{12}$ is hydrogen or lower alkyl; and
    (C) $R^{13}$ is lower alkyl;
(b) $R^2$ is hydrogen;
(c) $R^3$ is —$OR^{14}$, wherein $R^{14}$ is selected from the group consisting of:
  (1) lower alkyl,
  (2) lower halogenalkyl,
  (3) cycloalkyl,
  (4) lower cycloalkylalkyl,
  (5) lower heterocyclylalkyl,
  (6) lower heteroarylalkyl,
  (7) lower alkoxyalkyl, and
  (8) lower hydroxyalkyl; and
  (9) —$NR^{15}R^{16}$, wherein either: (A) $R^{15}$ is hydrogen or lower alkyl, and $R^{16}$ is selected from the group consisting of lower alkyl, cycloalkyl, lower cycloalkylalkyl, lower hydroxyalkyl and lower alkoxyalkyl; or
    (B) $R^{15}$ and $R^{16}$ together with the nitrogen atom to which they are attached form a heterocyclic ring selected from the group consisting of acetidine, pyrrolidine, piperidine and azepane, wherein said heterocyclic ring is optionally substituted by alkoxy;
(d) $R^4$ is hydrogen or halogen;
(e) $R^5$ is selected from the group consisting of hydrogen, halogen, lower halogenalkyl, lower halogenalkoxy, and cyano;
(f) $R^6$ is selected from the group consisting of hydrogen, halogen, lower halogenalkyl, lower halogenalkoxy, and cyano.
(g) $R^7$ is selected from the group consisting of hydrogen, halogen, lower halogenalkyl, lower halogenalkoxy and cyano; and
(h) $R^8$ is hydrogen or halogen.

Preferred are the compounds of formula I of the invention, wherein $R^1$ is cycloalkyl which is optionally substituted by a substituent selected from the group consisting of hydroxy, lower alkoxy and lower hydroxyalkyl; and more preferably compounds of formula I wherein $R^1$ is cycloalkyl substituted by hydroxy. More preferably, $R^1$ is cyclohexyl which is optionally substituted by a substituent selected from the group consisting of hydroxy, lower alkoxy and lower hydroxyalkyl. Most preferably, $R^1$ is cyclohexyl substituted by hydroxy.

Further preferred are compounds of formula I according to the present invention, wherein $R^1$ is —$CH_2$—$(CR^9R^{10})_m$-cycloalkyl, wherein: the cycloalkyl is optionally substituted by hydroxy or lower hydroxyalkyl; m is 0 or 1; $R^9$ is selected from the group consisting of hydrogen, lower alkyl and cycloalkyl; and $R^{10}$ is selected from the group consisting of hydrogen, hydroxy and lower alkoxy.

More preferred are compounds of formula I, wherein $R^1$ is —$CH_2$—$(CR^9R^{10})_m$-cycloalkyl, wherein m is 1; $R^9$ is hydrogen or lower alkyl; and $R^{10}$ is hydroxy.

Also preferred are compounds of formula I according to the invention, wherein $R^1$ is —$CH_2$—$(CR^9R^{10})_m$-cycloalkyl, wherein the cycloalkyl is substituted by hydroxy or lower hydroxyalkyl and m is 0.

Furthermore, compounds of formula I according to the invention are preferred, wherein $R^1$ is piperidinyl.

Another group of preferred compounds of formula I of the present invention are those, wherein $R^3$ is —$OR^{14}$, wherein $R^{14}$ is selected from the group consisting of lower alkyl, lower halogenalkyl, cycloalkyl, lower cycloalkylalkyl, lower heterocyclylalkyl, lower heteroarylalkyl, lower alkoxyalkyl, and lower hydroxyalkyl. More preferably are the compounds of formula I wherein $R^3$ is —$OR^{14}$ and $R^{14}$ is lower alkyl or cyloalkyl.

Further preferred are compounds of formula I of the present invention, wherein $R^3$ is —$OR^{14}$ and $R^{14}$ is lower alkoxyalkyl or lower hydroxyalkyl.

Especially preferred are compounds of formula I of the invention, wherein $R^3$ is —$OR^{14}$ and $R^{14}$ is 2-methoxyethyl.

Also preferred are compounds of formula I, wherein $R^3$ is —$OR^{14}$ and $R^{14}$ is selected from the group consisting of lower halogenalkyl, lower cycloalkylalkyl, lower heterocyclylalkyl and lower heteroarylalkyl.

More preferred are compounds of formula I, wherein $R^3$ is —$OR^{14}$ and $R^{14}$ is lower halogenalkyl, especially wherein $R^{14}$ is 2,2,2-trifluoroethyl.

In more preferred embodiments, $R^3$ is —$OR^{14}$ and $R^{14}$ is lower heterocyclylalkyl. Especially preferred are compounds of formula I, wherein $R^{14}$ is lower tetrahydrofuranylalkyl.

Further preferred are compounds of formula I, wherein $R^3$ is —$OR^{14}$ and $R^{14}$ is lower heteroarylalkyl. Especially preferred are the compounds of formula I, wherein $R^{14}$ is selected from the group consisting of lower pyridylalkyl, lower pyrimidinylalkyl, lower pyrazinylalkyl and lower pyridazinylalkyl.

Another group of preferred compounds of formula I of the present invention are those, wherein $R^3$ is —$NR^{15}R^{16}$ and wherein $R^{15}$ is hydrogen or lower alkyl and $R^{16}$ is selected from the group consisting of lower alkyl, cycloalkyl, lower cycloalkylalkyl, lower hydroxyalkyl and lower alkoxyalkyl; or alternatively $R^{15}$ and $R^{16}$ together with the nitrogen atom to which they are attached form a heterocyclic ring selected from the group consisting of acetidine, pyrrolidine, piperidine and azepane, said heterocyclic ring being optionally substituted by alkoxy.

Preferably, $R^3$ is —$NR^{15}R^{16}$, wherein $R^{15}$ is hydrogen or lower alkyl and $R^{16}$ is selected from the group consisting of lower alkyl, cycloalkyl, lower cycloalkylalkyl, lower hydroxyalkyl and lower alkoxyalkyl.

In other specific embodiments, compounds of formula I of the present invention are preferred, wherein $R^3$ is —$NR^{15}R^{16}$ and $R^{15}$ and $R^{16}$ together with the nitrogen atom to which they are attached form a heterocyclic ring selected from the group consisting of acetidine, pyrrolidine, piperidine and azepane, wherein said heterocyclic ring is optionally substituted by alkoxy.

Further preferred compounds of formula I according to the present invention are those, wherein $R^6$ is selected from the group consisting of halogen, lower halogenalkyl, lower halogenalkoxy and cyano.

Most preferably, $R^6$ is selected from the group consisting of fluoro, chloro, bromo, trifluoromethyl and trifluoromethoxy. Especially preferred are compounds, wherein $R^6$ is trifluoromethoxy.

Also preferred are compounds of formula I according to the present invention, wherein $R^4$, $R^5$, $R^7$ and $R^8$ are hydrogen.

In more specific embodiments, preferred compounds of formula I include the following:

5-azepan-1-yl-6-(4-fluoro-phenyl)-pyrazine-2-carboxylic acid (2-cyclopropyl-2-hydroxy-propyl)-amide, 6-(4-chloro-phenyl)-5-piperidin-1-yl-pyrazine-2-carboxylic acid (2-cyclopropyl-2-hydroxy-propyl)-amide, 6-(4-chloro-phenyl)-5-piperidin-1-yl-pyrazine-2-carboxylic acid ((S)-2-cyclopropyl-2-hydroxy-propyl)-amide, 6-(4-chloro-phenyl)-5-piperidin-1-yl-pyrazine-2-carboxylic acid ((R)-2 cyclopropyl-2-hydroxy-propyl)-amide, 6-(4-chloro-phenyl)-5-pyrrolidin-1-yl-pyrazine-2-carboxylic acid ((R)-2-cyclopropyl-2-hydroxy-propyl)-amide, 5-azepan-1-yl-6-(4-chloro-phenyl)-pyrazine-2-carboxylic acid ((R)-2-cyclopropyl-2-hydroxy-propyl)-amide, 6-(4-chloro-phenyl)-5-[(2-methoxy-ethyl)-methyl-amino]-pyrazine-2-carboxylic acid ((R)-2-cyclopropyl-2-hydroxy-propyl)-amide, 6-(4-chloro-phenyl)-5-[methyl-(3-methyl-butyl)-amino]-pyrazine-2-carboxylic acid ((R)-2-cyclopropyl-2-hydroxy-propyl)-amide, 6-(4-chloro-phenyl)-5-(hexyl-methyl-amino)-pyrazine-2-carboxylic acid ((R)-2-cyclopropyl-2-hydroxy-propyl)-amide, 6-(4-chloro-phenyl)-5-(cyclopropylmethyl-amino)-pyrazine-2-carboxylic acid ((R)-2-cyclopropyl-2-hydroxy-propyl)-amide, 5-azetidin-1-yl-6-(4-chloro-phenyl)-pyrazine-2-carboxylic acid ((R)-2-cyclopropyl-2-hydroxy-propyl)-amide, 6-(4-chloro-phenyl)-5-(3-methoxy-azetidin-1-yl)-pyrazine-2-carboxylic acid ((R)-2-cyclopropyl-2-hydroxy-propyl)-amide, 6-(4-chloro-phenyl)-5-(3-ethoxy-azetidin-1-yl)-pyrazine-2-carboxylic acid ((R)-2-cyclopropyl-2-hydroxy-propyl)-amide, 6-(4-chloro-phenyl)-5-(cyclopropyl-methyl-amino)-pyrazine-2-carboxylic acid ((R)-2-cyclopropyl-2-hydroxy-propyl)-amide, 6-(4-chloro-phenyl)-5-(cyclopropylmethyl-methyl-amino)-pyrazine-2-carboxylic acid ((R)-2-cyclopropyl-2-hydroxy-propyl)-amide, 6-(4-chloro-phenyl)-5-[(2-hydroxy-ethyl)-methyl-amino]-pyrazine-2-carboxylic acid ((R)-2-cyclopropyl-2-hydroxy-propyl)-amide, 6-phenyl-5-piperidin-1-yl-pyrazine-2-carboxylic acid (2-cyclopropyl-2-hydroxy-propyl)-amide, 5-[methyl-(3-methyl-butyl)-amino]-6-(4-trifluoromethyl-phenyl)-pyrazine-2-carboxylic acid ((R)-2-cyclopropyl-2-hydroxy-propyl)-amide, 5-(cyclopropylmethyl-methyl-amino)-6-(4-trifluoromethyl-phenyl)-pyrazine-2-carboxylic acid ((R)-2-cyclopropyl-2-hydroxy-propyl)-amide, 5-(cyclopropyl-methyl-amino)-6-(4-trifluoromethyl-phenyl)-pyrazine-2-carboxylic acid ((R)-2-cyclopropyl-2-hydroxy-propyl)-amide, 5-(cyclopropyl-methyl-amino)-6-(4-trifluoromethoxy-phenyl)-pyrazine-2-carboxylic acid ((1R,2R)-2-hydroxy-cyclohexyl)-amide, 5-(cyclopropylmethyl-methyl-amino)-6-(4-trifluoromethoxy-phenyl)-pyrazine-2-carboxylic acid ((1R,2R)-2-hydroxy-cyclohexyl)-amide, 5-[methyl-(3-methyl-butyl)-amino]-6-(4-trifluoromethoxy-phenyl)-pyrazine-2-carboxylic acid ((1R,2R)-2-hydroxy-cyclohexyl)-amide, 5-(cyclopropyl-methyl-amino)-6-(4-trifluoromethoxy-phenyl)-pyrazine-2-carboxylic acid ((R)-2-cyclopropyl-2-hydroxy-propyl)-amide, 5-(cyclopropylmethyl-methyl-amino)-6-(4-trifluoromethoxy-phenyl)-pyrazine-2-carboxylic acid ((R)-2-cyclopropyl-2-hydroxy-propyl)-amide, 6-(4-chloro-phenyl)-5-(2-methoxy-ethoxy)-pyrazine-2-carboxylic acid ((S)-2-cyclopropyl-2-hydroxy-propyl)-amide, 6-(4-chloro-phenyl)-5-(2-methoxy-ethoxy)-pyrazine-2-carboxylic acid ((R)-2-cyclopropyl-2-hydroxy-propyl)-amide, 6-(4-chloro-phenyl)-5-cyclopentylmethoxy-pyrazine-2-carboxylic acid (2-cyclopropyl-2-hydroxy-propyl)-amide, 6-(4-chloro-phenyl)-5-cyclopentylmethoxy-pyrazine-2-carboxylic acid ((1R,2R)-2-hydroxy-cyclohexyl)-amide, 6-(4-chloro-phenyl)-5-(2-methoxy-ethoxy)-pyrazine-2-carboxylic acid ((1R,2R)-2-hydroxy-cyclohexyl)-amide, 6-(2,4-dichloro-phenyl)-5-(2-methoxy-ethoxy)-pyrazine-2-carboxylic acid (2-cyclopropyl-2-hydroxy-propyl)-amide, 6-(2,4-dichloro-phenyl)-5-(2-methoxy-ethoxy)-pyrazine-2-carboxylic acid ((1R,2R)-2-hydroxy-cyclohexyl)-amide, 6-(4-chloro-phenyl)-5-(3-methoxy-propoxy)-pyrazine-2-carboxylic acid (2-cyclopropyl-2-hydroxy-propyl)-amide, 6-(4-chloro-phenyl)-5-(3-methyl-butoxy)-pyrazine-2-carboxylic acid (2-cyclopropyl-2-hydroxy-propyl)-amide, 6-(4-chloro-phenyl)-5-(3-methyl-butoxy)-pyrazine-2-carboxylic acid ((1R,2R)-2-hydroxy-cyclohexyl)-amide, 6-(4-chloro-phenyl)-5-(3-methyl-butoxy)-pyrazine-2-carboxylic acid piperidin-1-ylamide, 6-(4-chloro-phenyl)-5-(2-methoxy-ethoxy)-pyrazine-2-carboxylic acid (1-hydroxymethyl-cyclopropyl)-amide, 6-(4-chloro-phenyl)-5-(2-methoxy-ethoxy)-pyrazine-2-carboxylic acid piperidin-1-ylamide, 6-(4-chloro-phenyl)-5-(2-methoxy-ethoxy)-pyrazine-2-carboxylic acid (1-hydroxy-cyclopropylmethyl)-amide, 5-cyclopropylmethoxy-6-(4-fluoro-phenyl)-pyrazine-2-carboxylic acid (2-cyclopropyl-2-hydroxy-propyl)-amide, 6-(4-fluoro-phenyl)-5-(tetrahydro-furan-2-ylmethoxy)-pyrazine-2-carboxylic acid (2-cyclopropyl-2-hydroxy-propyl)-amide, 6-(4-chloro-phenyl)-5-[(R)-1-(tetrahydro-furan-2-yl)methoxy]-pyrazine-2-carboxylic acid ((R)-2-cyclopropyl-2-hydroxy-propyl)-amide, 6-(4-chloro-phenyl)-5-(2-methoxy-ethoxy)-pyrazine-2-carboxylic acid (2,2-dicyclopropyl-2-hydroxy-ethyl)-amide, 6-(4-chloro-phenyl)-5-methoxy-pyrazine-2-carboxylic acid (2,2-dicyclopropyl-2-hydroxy-ethyl)-amide, 6-(4-chloro-phenyl)-5-(2-methoxy-ethoxy)-pyrazine-2-carboxylic acid (1-hydroxymethyl-cyclopropylmethyl)-amide, 6-(4-chloro-phenyl)-5-[(S)-1-(tetrahydro-furan-2-yl)methoxy]-pyrazine-2-carboxylic acid ((R)-2-cyclopropyl-2-hydroxy-propyl)-amide, 6-(4-chloro-phenyl)-5-(2-hydroxy-ethoxy)-pyrazine-2-carboxylic acid ((R)-2-cyclopropyl-2-hydroxy-propyl)-amide, 5-butoxy-6-(4-chloro-phenyl)-pyrazine-2-carboxylic acid ((R)-2-cyclopropyl-2-hydroxy-propyl)-amide, 6-(4-chloro-phenyl)-5-(2,2,2-trifluoro-ethoxy)-pyrazine-2-carboxylic acid ((R)-2-cyclopropyl-2-hydroxy-propyl)-amide, 6-(4-chloro-phenyl)-5-(2,2,2-trifluoro-1-methyl-ethoxy)-pyrazine-2-carboxylic acid ((R)-2-cyclopropyl-2-hydroxy-propyl)-amide, 5-cyclopropylmethoxy-6-(4-fluoro-phenyl)-pyrazine-2-carboxylic acid ((R)-2-cyclopropyl-2-hydroxy-propyl)-amide, 5-cyclopropylmethoxy-6-(4-fluoro-phenyl)-pyrazine-2-carboxylic acid ((S)-2-cyclopropyl-2-hydroxy-propyl)-amide, 6-(4-fluoro-phenyl)-5-(2,2,2-trifluoro-ethoxy)-pyrazine-2-carboxylic acid ((R)-2-cyclopropyl-2-hydroxy-propyl)-amide, 6-(4-fluoro-phenyl)-5-(2,2,2-trifluoro-ethoxy)-pyrazine-2-carboxylic acid ((1R,2R)-2-hydroxy-cyclohexyl)-amide, 6-(4-fluoro-phenyl)-5-(2-methoxy-ethoxy)-pyrazine-2-carboxylic acid ((1R,2R)-2-hydroxy-cyclohexyl)-amide, 5-(2-methoxy-ethoxy)-6-(4-trifluoromethyl-phenyl)-pyrazine-2-carboxylic acid (2-cyclopropyl-2-hydroxy-propyl)-amide, 5-cyclopentylmethoxy-6-(4-trifluoromethyl-phenyl)-pyrazine-2-carboxylic acid (2-cyclopropyl-2-hydroxy-propyl)-amide, 5-(3-methoxy-propoxy)-6-(4-trifluoromethyl-phenyl)-pyrazine-2-carboxylic acid (2-cyclopropyl-2-hydroxy-propyl)-amide, 5-[(R)-1-(tetrahydro-furan-2-yl)methoxy]-6-(4-trifluoromethyl-phenyl)-pyrazine-2-carboxylic acid (2-cyclopropyl-2-hydroxy-propyl)-amide, 5-(3-methyl-butoxy)-6-(4-trifluoromethyl-phenyl)-pyrazine-2-carboxylic acid (2-cyclopropyl-2-hydroxy-propyl)-amide, 5-butoxy-6-(4-trifluoromethyl-phenyl)-pyrazine-2-carboxylic acid (2-cyclopropyl-2-hydroxy-propyl)-amide, 5-[(S)-1-(tetrahydro-furan-2-yl)methoxy]-6-(4-trifluoromethyl-phenyl)-pyrazine-2-carboxylic acid ((R)-2-cyclopropyl-2-hydroxy-propyl)-amide, 5-(2,2,2-trifluoro-ethoxy)-6-(4-trifluoromethyl-phenyl)-pyrazine-2-carboxylic acid ((R)-2-cyclopropyl-2-hydroxy-propyl)-amide, 5-(2-methoxy-ethoxy)-6-(4-trifluoromethoxy-phenyl)-pyrazine-2-carboxylic acid ((1R,2R)-2-hydroxy-cyclohexyl)-amide, 5-cyclopropylmethoxy-6-(4-trifluoromethoxy-phenyl)-pyrazine-2-carboxylic acid ((1R,2R)-2-hydroxy-cyclohexyl)-amide, 5-(2-methoxy-ethoxy)-6-(4-trifluoromethoxy-phenyl)-pyrazine-2-carboxylic acid ((R)-2-cyclopropyl-2-hydroxy-propyl)-amide 5-cyclopropylmethoxy-6-(4-trifluoromethoxy-phenyl)-pyrazine-2-carboxylic acid ((R)-2-cyclopropyl-2-hydroxy-propyl)-amide, 6-(4-fluoro-phenyl)-5-(pyridin-2-ylmethoxy)-pyrazine-2-carboxylic acid ((R)-2-cyclopropyl-2-hydroxy-propyl)-amide, 6-(4-fluoro-phenyl)-5-(pyrimidin-2-ylmethoxy)-pyrazine-2-carboxylic acid ((R)-2-cyclopropyl-2-hydroxy-propyl)-amide, 6-(4-fluoro-phenyl)-5-(pyridazin-3-ylmethoxy)-pyrazine-2-carboxylic acid ((R)-2-cyclopropyl-2-hydroxy-propyl)-amide, 6-(4-fluoro-phenyl)-5-(pyrimidin-4-ylmethoxy)-pyrazine-2-carboxylic acid ((R)-2-cyclopropyl-2-hydroxy-propyl)-amide, 6-(4-fluoro-phenyl)-5-(pyrazin-2-ylmethoxy)-pyrazine-2-carboxylic acid ((R)-2-cyclopropyl-2-hydroxy-propyl)-amide, 6-(4-chloro-phenyl)-5-(pyrimidin-2-ylmethoxy)-pyrazine-2-carboxylic acid ((R)-2-cyclopropyl-2-hydroxy-propyl)-amide, 5-(pyrimidin-2-ylmethoxy)-6-(4-trifluoromethoxy-phenyl)-pyrazine-2-carboxylic acid ((R)-2-cyclopropyl-2-hydroxy-propyl)-amide, 6-(4-fluoro-phenyl)-5-(pyridin-2-ylmethoxy)-pyrazine-2-carboxylic acid ((1R,2R)-2-hydroxy-cyclohexyl)-amide, 6-(4-fluoro-phenyl)-5-(pyrimidin-2-ylmethoxy)-pyrazine-2-carboxylic acid ((1R,2R)-2-hydroxy-cyclohexyl)-amide, 5-(pyridin-2-ylmethoxy)-6-(4-trifluoromethoxy-phenyl)-pyrazine-2-carboxylic acid ((1R,2R)-2-hydroxy-cyclohexyl)-amide, 5-(pyrimidin-2-ylmethoxy)-6-(4-trifluoromethoxy-phenyl)-pyrazine-2-carboxylic acid ((1R,2R)-2-hydroxy-cyclohexyl)-amide, 5-(pyrimidin-4-ylmethoxy)-6-(4-trifluoromethoxy-phenyl)-pyrazine-2-carboxylic acid ((1R,2R)-2-hydroxy-cyclohexyl)-amide, 5-(pyrazin-2-ylmethoxy)-6-(4-trifluoromethoxy-phenyl)-pyrazine-2-carboxylic acid ((1R,2R)-2-hydroxy-cyclohexyl)-amide, 6-(4-chloro-phenyl)-5-(pyrimidin-2-ylmethoxy)-pyrazine-2-carboxylic acid ((S)-2-cyclopropyl-2-hydroxy-propyl)-amide, and any pharmaceutically acceptable salt thereof.

Another more specific group of preferred compounds of formula I are the following:

6-(4-chloro-phenyl)-5-[methyl-(3-methyl-butyl)-amino]-pyrazine-2-carboxylic acid ((R)-2-cyclopropyl-2-hydroxy-propyl)-amide, 6-(4-chloro-phenyl)-5-(cyclopropylmethyl-methyl-amino)-pyrazine-2-carboxylic acid ((R)-2-cyclopropyl-2-hydroxy-propyl)-amide, 5-(cyclopropylmethyl-methyl-amino)-6-(4-trifluoromethoxy-phenyl)-pyrazine-2-carboxylic acid ((1R,2R)-2-hydroxy-cyclohexyl)-amide, 5-[methyl-(3-methyl-butyl)-amino]-6-(4-trifluoromethoxy-phenyl)-pyrazine-2-carboxylic acid ((1R,2R)-2-hydroxy-cyclohexyl)-amide, 5-(cyclopropyl-methyl-amino)-6-(4-trifluoromethoxy-phenyl)-pyrazine-2-carboxylic acid ((R)-2-cyclopropyl-2-hydroxy-propyl)-amide, 5-(cyclopropylmethyl-methyl-amino)-6-(4-trifluoromethoxy-phenyl)-pyrazine-2-carboxylic acid ((R)-2-cyclopropyl-2-hydroxy-propyl)-amide, 6-(4-chloro-phenyl)-5-(2-methoxy-ethoxy)-pyrazine-2-carboxylic acid ((R)-2-cyclopropyl-2-hydroxy-propyl)-amide, 6-(4-chloro-phenyl)-5-(2-methoxy-ethoxy)-pyrazine-2-carboxylic acid ((1R,2R)-2-hydroxy-cyclohexyl)-amide, 5-cyclopropylmethoxy-6-(4-fluoro-phenyl)-pyrazine-2-carboxylic acid (2-cyclopropyl-2-hydroxy-propyl)-amide, 6-(4-chloro-phenyl)-5-[(R)-1-(tetrahydro-furan-2-yl)methoxy]-pyrazine-2-carboxylic acid ((R)-2-cyclopropyl-2-hydroxy-propyl)-amide, 6-(4-chloro-phenyl)-5-[(S)-1-(tetrahydro-furan-2-yl)methoxy]-pyrazine-2-carboxylic acid ((R)-2-cyclopropyl-2-hydroxy-propyl)-amide, 5-butoxy-6-(4-chloro-phenyl)-pyrazine-2-carboxylic acid ((R)-2-cyclopropyl-2-hydroxy-propyl)-amide, 6-(4-chloro-phenyl)-5-(2,2,2-trifluoro-ethoxy)-pyrazine-2-carboxylic acid ((R)-2-cyclopropyl-2-hydroxy-propyl)-amide, 5-cyclopropylmethoxy-6-(4-fluoro-phenyl)-pyrazine-2-carboxylic acid ((R)-2-cyclopropyl-2-hydroxy-propyl)-amide, 5-(2-methoxy-ethoxy)-6-(4-trifluoromethyl-phenyl)-pyrazine-2-carboxylic acid (2-cyclopropyl-2-hydroxy-propyl)-amide, 5-(2,2,2-trifluoro-ethoxy)-6-(4-trifluoromethyl-phenyl)-pyrazine-2-carboxylic acid ((R)-2-cyclopropyl-2-hydroxy-propyl)-amide, 5-(2-methoxy-ethoxy)-6-(4-trifluoromethoxy-phenyl)-pyrazine-2-carboxylic acid ((R)-2-cyclopropyl-2-hydroxy-propyl)-amide 5-cyclopropylmethoxy-6-(4-trifluoromethoxy-phenyl)-pyrazine-2-carboxylic acid ((R)-2-cyclopropyl-2-hydroxy-propyl)-amide, 6-(4-fluoro-phenyl)-5-(pyridin-2-ylmethoxy)-pyrazine-2-carboxylic acid ((R)-2-cyclopropyl-2-hydroxy-propyl)-amide, 6-(4-fluoro-phenyl)-5-(pyrazin-2-ylmethoxy)-pyrazine-2-carboxylic acid ((R)-2-cyclopropyl-2-hydroxy-propyl)-amide, 6-(4-chloro-phenyl)-5-(pyrimidin-2-ylmethoxy)-pyrazine-2-carboxylic acid ((R)-2-cyclopropyl-2-hydroxy-propyl)-amide, and any pharmaceutically acceptable salt thereof.

Especially preferred are the compounds of formula I which are selected from the group consisting of:

5-(cyclopropylmethyl-methyl-amino)-6-(4-trifluoromethoxy-phenyl)-pyrazine-2-carboxylic acid ((1R,2R)-2-hydroxy-cyclohexyl)-amide, 6-(4-chloro-phenyl)-5-(2-methoxy-ethoxy)-pyrazine-2-carboxylic acid ((R)-2-cyclopropyl-2-hydroxy-propyl)-amide, 6-(4-chloro-phenyl)-5-(2,2,2-trifluoro-ethoxy)-pyrazine-2-carboxylic acid ((R)-2-cyclopropyl-2-hydroxy-propyl)-amide, 5-cyclopropylmethoxy-6-(4-fluoro-phenyl)-pyrazine-2-carboxylic acid ((R)-2-cyclopropyl-2-hydroxy-propyl)-amide, 5-cyclopropylmethoxy-6-(4-trifluoromethoxy-phenyl)-pyrazine-2-carboxylic acid ((R)-2-cyclopropyl-2-hydroxy-propyl)-amide, and any pharmaceutically acceptable salt thereof.

The present invention also relates to a process for the manufacture of the compounds of formula I as defined above, which process comprises:

coupling a compound of formula

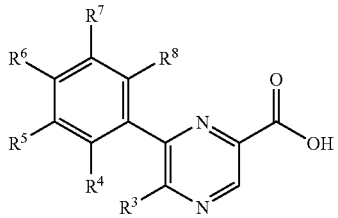

II wherein $R^3$ to $R^8$ are as defined herein before, with an amine of the formula <p style="text-align:center">H—NR$^1$R$^2$      III</p> wherein $R^1$ and $R^2$ are as defined herein before, with the help of an activating agent under basic conditions, and, if desired, converting the resulting compound of formula I into a pharmaceutically acceptable salt thereof.

Activating agents include coupling agents for the reaction of compounds of formula II with amines of formula III as for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). A preferred coupling agent is TBTU. Furthermore, the term "activating agent" also includes (1-chloro-2-methyl-propenyl)-dimethylamine which converts the acid of formula II into an acid chloride, which is then reacted with the amine of formula III under basic conditions to obtain the compound of formula I.

Suitable bases include triethylamine, diisopropylethylamine and, preferably, Hünig's base.

Alternatively, the present invention also relates to a process for the manufacture of compounds of formula I as defined above, which process comprises coupling a compound of formula

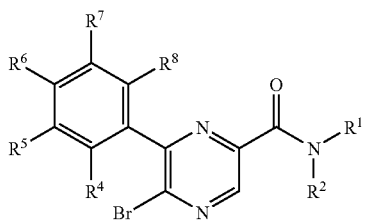

IV wherein $R^1$, $R^2$ and $R^4$ to $R^8$ are as defined herein before, with an amine of the formula <p style="text-align:center">H—NR$^{15}$R$^{16}$      V</p> wherein $R^{15}$ and $R^{16}$ are as defined herein before, with the help of an activating agent under basic conditions, and, if desired, converting the resulting compound of formula I into a pharmaceutically acceptable salt thereof.

Alternatively, the present invention also relates to a process for the manufacture of compounds of formula I as defined above, which process comprises coupling a compound of formula

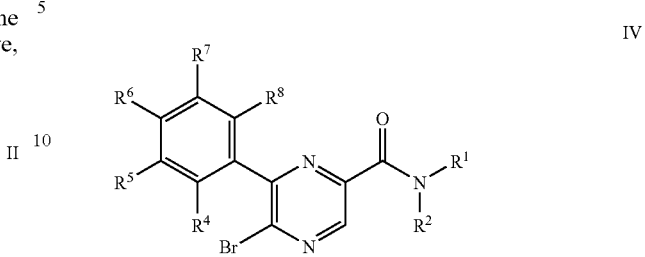

IV wherein $R^1$, $R^2$ and $R^4$ to $R^8$ are as defined herein before, with an alcohol of the formula <p style="text-align:center">R$^{14}$—OH      VI</p> wherein $R^{14}$ is as defined herein before, in the presence of a metal hydride or metal carbonate, and, if desired, converting the resulting compound of formula I into a pharmaceutically acceptable salt thereof.

Preferably, the metal hydride is sodium hydride. A preferred metal carbonate is cesium carbonate.

Thus, the compounds of formula I can be manufactured by the methods provided herein, given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The synthesis of compounds of general structure I, can be accomplished according to schemes 1 to 3.

A compound of formula 1 can be transformed to a compound of formula 2 by reaction with aryl boronic acids (exemplified but by no means restricted to phenylboronic acid; 4-fluorophenylboronic acid; 4-chlorophenylboronic acid, (4-trifluoromethyl)phenylboronic acid or 4-trifluoromethoxyphenylboronic acid) in an appropriate solvent such as 1,2-dimethoxyethane in the presence of a suitable catalyst such as tetrakis(triphenylphosphine) palladium (0) and a suitable base such as sodium carbonate at temperatures typically ranging from 0° C. to 120° C.; a protocol commonly known as the Suzuki reaction.

Transformation of a compound of formula 2 to a compound of formula 3 can be effected by palladium catalyzed insertion of carbon monoxide into the aryl-bromine bond in a solvent containing an alcohol such as methanol under an atmosphere of carbon monoxide at pressures typically ranging from 1 bar to 200 bar and temperatures typically ranging from 20° C. to 150° C.

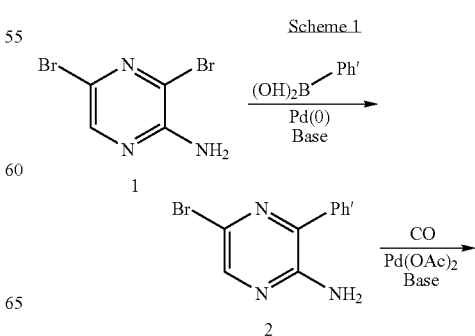

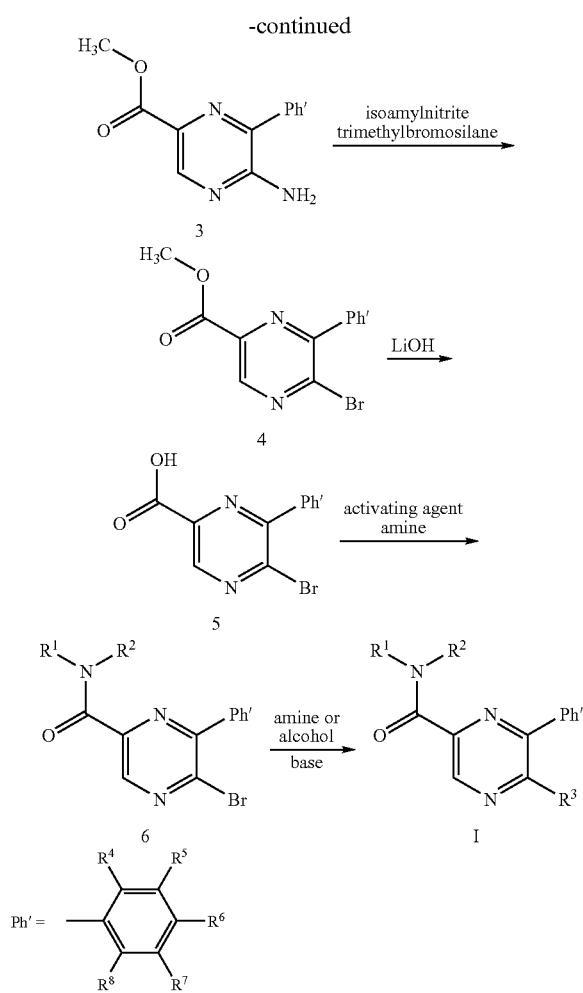

Compounds of the formula 3 can be converted to compounds of the formula 4 by reaction with a source of nitrite, preferably isoamyl nitrite in the presence of a source of bromide such as metal bromides or bromine containing solvents such as dibromo-methane and an activating agent such as hydrobromic acid or trimethylbromosilane at temperatures ranging from −20° C. to 80° C., typically at ambient temperature.

Saponification of compounds of formula 4 to compounds of formula 5 can be carried out in the presence of a suitable base such as a metal hydroxide, preferably lithium hydroxide, in an appropriate solvent such as tetrahydrofuran and mixtures thereof with water at temperatures ranging from 0° C. to 100° C., preferably at 20° C.

Coupling of compounds of general formula 5 with amines to give compounds of general formula 6 can be carried out by methods used for the formation of peptide bonds. In one particular aspect of the invention compounds of the general formula V can be converted to their acid chlorides by reaction with (1-chloro-2-methyl-propenyl)-dimethyl-amine in an inert solvent such as dichloromethane and subsequently coupled to amines in the presence of suitable bases such as triethylamine or Huenig's base.

Compounds of general formula 6 can be reacted with a wide variety of alcohols and amines in suitable solvents such as dimethylformamide or dimethylsulfoxide in the presence of a suitable base, preferably an excess of the amine itself or tertiary amine bases exemplified by triethylamine, Huenig's base or N,N,N',N'-tetramethylguanidine, in the case of reaction with amines or in case of reaction with alcohols, in the presence of suitable bases such as metal hydrides, preferably sodium hydride or metal carbonates such as cesium carbonate to yield compounds of general formula I.

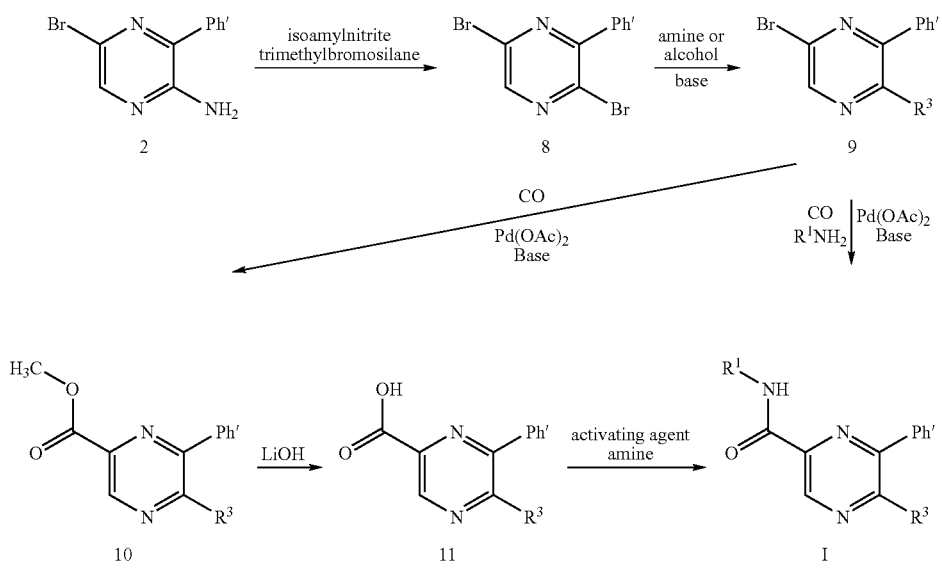

Alternatively compounds of general formula 2 can be transformed to compounds of general formula 8 by essentially the same conditions as described above for the conversion of compounds of general formula 3 to compounds of general formula 4. Compounds of formula 8 can be reacted with amines or alcohols under conditions described above for conversion of compounds of formula 6 to compounds of formula I yielding preferentially compounds of formula 9. Further transformation of compounds of general formula 9 to compounds of general formula I can be accomplished via intermediates of general formula 10, and compounds of general formula 11 using the methods described for the transformation of compounds of general formula 2 to compounds of general formula 3 and of compounds of general formula 4 to compounds of general formula 6 via compounds of general formula 5.

In a further aspect of the invention compounds of general formula 9 can be transformed to compounds of general formula I directly by palladium catalyzed carbonylation in the presence of appropriate amines under condition otherwise similar to the above described transformations of compounds of general formula 2 to compounds of general formula 3.

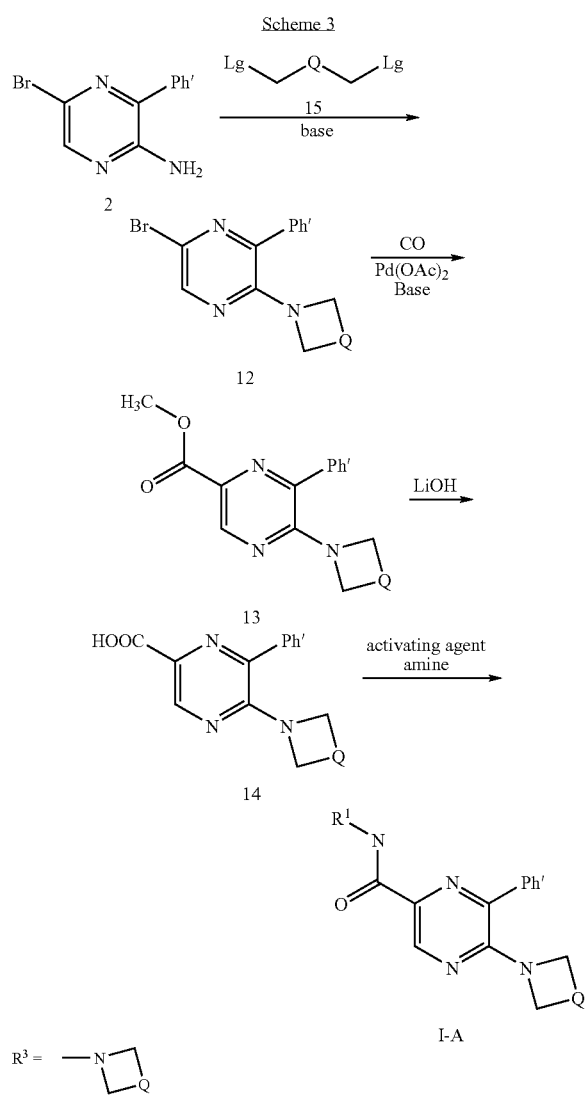

Compounds of general formula 2 can be transformed into compounds of general formula 12 by reaction with compounds of general formula 15 in which the abbreviation Lg stands for a suitable leaving group such as a halogen group or a mesylate group and Q stands for a carbon chain consisting of 2 to 3 methylene units or a chain consisting of a methylene unit an oxygen atom and an other methylene unit. Further transformation into compounds of general formula I-A can be carried out in analogy to the transformation of compounds of general formula 9 to compounds of general formula I.

The invention further relates to compounds of formula I as defined above, when manufactured according to a process as defined above.

Some compounds of formula I may possess asymmetric centres and are therefore capable of existing in more than one stereoisomeric form. The invention thus also relates to compounds in substantially pure isomeric form at one or more asymmetric centres as well as mixtures, including racemic mixtures, thereof. Such isomers may be prepared by asymmetric synthesis, for example using chiral intermediates, or mixtures may be resolved by conventional methods, e.g. chromatography (chromatography with a chiral adsorbens or eluent), or use of a solving agent.

It will be appreciated, that the compounds of general formula I in this invention may be derivatized at functional groups to provide derivatives which are capable of conversion back to the parent compound in vivo.

As described above, compounds of formula I or pharmaceutically acceptable salts thereof can be used as medicaments for the treatment and/or prophylaxis of diseases which are associated with the modulation of the CB1 receptors.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with the modulation of CB1 receptors.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments for the treatment and/or prophylaxis of diseases which are associated with the modulation of CB1 receptors. Such medicaments comprise a compound as defined above.

In this context, the expression 'diseases associated with modulation of CB1 receptors' means diseases which can be treated and/or prevented by modulation of CB1 receptors. Such diseases encompass, but are not limited to, psychic disorders, especially anxiety, psychosis, schizophrenia, depression, abuse of psychotropes, for example for the abuse and/or dependence of a substances, including alcohol dependency and nicotine dependency, neuropathies, multiple sclerosis, migraine, stress, epilepsy, dyskinesias, Parkinson's disease, amnesia, cognitive disorders, memory deficits, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, neuroinflammation, in particular in atherosclerosis, or the Guillain-Barré syndrome, viral encephalitis, cerebral vascular incidents and cranial trauma.

In preferred embodiments the diseases associated with the modulation of CB1 receptors that can be treated by the compounds of the present invention include eating disorders, obesity, diabetes type II or non insulin dependent diabetes (NIDD), neuroinflammation, diarrhea, abuse and/or dependence of a substances, including alcohol dependency and nicotine dependency. In more preferred embodiments the diseases treated with the compounds of the present invention are eating disorders, obesity, diabetes type II or non insulin dependent diabetes (NIDD), abuse and/or dependence of a substances, including alcohol dependency and nicotine dependency, with obesity being especially preferred.

It is a further preferred object to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

It is a further preferred object to provide a method of treatment or prevention of Type II diabetes (non-insulin dependent diabetes mellitus (NIDDM) in a human which comprises administration of a therapeutically effective amount of a compound according to formula I in combination or association with a therapeutically effective amount of a lipase inhibitor, particularly, wherein the lipase inhibitor is orlistat. Also an object of the invention is the method as described above for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM) in a human which comprises administration of a therapeutically effective amount of a compound according to formula I in combination or association with a therapeutically effective amount of an anti-diabetic agent selected from the group consisting of 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331, and the like 5) DPP-IV-inhibitors such as LAF-237 (Vildagliptin) or MK-0431, and the like; 6) Glucokinase activators such as the compounds disclosed in e.g. WO 00/58293 A1, and the like. Also an object of the invention is the method as described above for the simultaneous, separate or sequential administration of a compound according to formula I and a therapeutically effective amount of an anti-diabetic agent such as 1) PPARγ agonists such as pioglitazone or rosiglitazone, and the like; 2) biguanides such as metformin, and the like; 3) sulfonylureas such as glibenclamide, and the like; 4) PPARα/γ agonists such as GW-2331 GW-2331 and the like; 5) DPP-IV-inhibitors such as LAF-237 (Vildagliptin) or MK-0431, and the like; 6) Glucokinase activators such as the compounds disclosed in e.g. WO 00/58293 A1, and the like.

It is a further preferred object to provide a method of treatment or prevention of dyslipidemias in a human which comprises administration of a therapeutically effective amount of a compound according to formula I in combination or association with a therapeutically effective amount of a lipid lowering agent such as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists. Also an object of the invention is the method as described above for the simultaneous, separate or sequential administration of a compound according to formula I and a therapeutically effective amount of a lipid lowering agent as 1) bile acid sequestrants such as cholestyramine, and the like; 2) HMG-CoA reductase inhibitors such as atorvastatin, and the like; 3) cholesterol absorption inhibitors such as ezetimibe, and the like; 4) CETP inhibitors such as torcetrapib, JTT 705, and the like; 5) PPARα-agonists such as beclofibrate, fenofibrate, and the like; 6) lipoprotein synthesis inhibitors such as niacin, and the like; and 7) niacin receptor agonists.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149-153, 1990; Morris, J. Neurosci. Methods 11:47-60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Learning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442-448, 2002; Campbell et al., Exp. Clin. Psychopharmacol. 8:312-25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior.

The following tests were carried out in order to determine the activity of the compounds of formula I:

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glass-fiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glass-fiber filters. Radioactivity on the filter was measured by liquid scintillation counting. The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature 1990, 346, 561-564 (CB1) and Nature 1993, 365, 61-65 (CB2) respectively. Adenylyl cyclase was stimulated using forskolin and measured by quantifying the amount of accumulated cyclic AMP. Concomitant activation of CB1 receptors by CB1 receptor agonists (e.g. CP-55,940 or (R)-WIN-55212-2) can attenuate the forskolin-induced accumulation of cAMP in a concentration dependent manner. This CB1 receptor mediated response can be antagonized by CB1 receptor antagonists such as the compounds of the invention.

The compounds of formula (I) show an excellent affinity for the CB1 receptor, determined with the experimental conditions described in Devane et. al. Mol. Pharmacol. 34 (1988) 605-613. The compounds of the present invention or their pharmaceutically acceptable salts are antagonists and selective for the CB1 receptor with affinites below $K_i=0.5$ µM, preferably below 200 nM, more preferably 1 nM to 100 nM. They exhibit at least a 10 fold selectivity against the CB2 receptor.

| Compound of Example | $K_i$ [µM] |
|---|---|
| Example 21 | 0.0354 |
| Example 27 | 0.0475 |
| Example 69 | 0.0122 |

Effect of CB1 Receptor Antagonist/Inverse Agonist on CP 55,940-Induced Hypothermia in NMRI Mice Animals Male NMRI mice were used in this study and were obtained from Research Consulting Company Ltd (RCC) of Füllinsdorf (Switzerland). Mice, weighing 30-31 g were used in this study. Ambient temperature is approximately 20-21° C. and relative humidity 55-65%. A 12 hours light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense no. 8528-20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

The in vivo activity of compounds of formula (I) was assessed for their ability to regulate feeding behavior by recording food consumption in food deprived animals.

Rats were trained to have access to food for 2 h per day and were food deprived for 22 h. When they were trained under this schedule, the amount of food taken every day during these 2 h food intake session was consistent day after day.

To test the ability of compounds of formula I to decrease food intake, 8 animals were used in a cross-over study. Rats were individually housed in Plexiglas boxes with a grid on the floor and a paper was placed below the cage floor to collect any spillage. A food dispenser (becher) filled with a pre-weighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. *$P<0.05$ compared to Saline-treated rats.

Furthermore the utility of compounds of formula I in diseases or disorders may be demonstrated in animal disease models that have been reported in the literature. The following are examples of such animal disease models: a) reduction of sweet food intake in marmosets (Behavioral Pharm, 1998, 9, 179-181); b) reduction of sucrose and ethanol intake in mice (Psychopharm. 1997, 132, 104-106); c) increased motor activity and place conditioning in rats (Psychopharm. 1998, 135, 324-332; Psychopharmacol 2000, 151: 25-30); d) spontaneous locomotor activity in mice (J. Pharm. Exp. Ther. 1996, 277, 586-594); e) reduction in opiate self-administration in mice (Sci. 1999, 283, 401-404).

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following examples serve to illustrate the present invention in more detail. They are, however, not intended to limit its scope in any manner.

EXAMPLES

The following are a list of abbreviations and/or acronyms with their corresponding definitions used in the following examples: HPLC=high performance liquid chromatography; TLC=thin layer chromatography; DMSO=dimethyl sulfoxide; CDCl$_3$ deuterated chloroform; MS=mass spectrometry; (M+H$^+$)=the molecular weight of the compound plus a proton; and ISP=ion spray, which is a modification of ESI (electrospray ionization). In addition, NMR data are reported in parts per million (δ) relative to internal tetramethylsilane and are referenced to the deuterium lock signal from the sample solvent (d$_6$-DMSO unless otherwise stated); coupling constants (j) are in Hertz, mp=melting point; and bp=boiling point.

Example 1

5-Azepan-1-yl-6-(4-fluoro-phenyl)-pyrazine-2-carboxylic acid (2-cyclopropyl-2-hydroxy-propyl)-amide To a solution of 0.050 g 5-bromo-6-(4-fluoro-phenyl)-pyrazine-2-carboxylic acid (2-cyclopropyl-2-hydroxy-propyl)-amide in 2 ml dimethylsulfoxide was added at room temperature 0.063 g hexamethyleneimine and the mixture was stirred at room temperature for 2 hours. The reaction mixture was partitioned between 10% aqueous citric acid and ethyl acetate. The phases were separated and the organic phase washed with 10% aqueous sodium bicarbonate and brine, dried over magnesium sulfate and evaporated. The residue was purified by chromatography on silica gel with a gradient of heptane to 25% ethyl acetate in heptane to yield 0.049 g of the title compound as white foam. MS (ISP) (M+H$^+$)=413.5.

The starting material was prepared as follows:

Example 1a

5-Bromo-3-(4-fluoro-phenyl)-pyrazin-2-ylamine

To a solution of 5.058 g of 3,5-dibromo-pyrazin-2-ylamine in 100.0 ml 1,2-dimethoxyethane was added at room temperature 1.156 g of tetrakis(triphenylphosphine) palladium (0) and stirred for 0.5 hours. To the resulting mixture was added a solution of 5.30 g sodium carbonate in 50.0 ml water and 3.078 g 4-fluorophenylboronic acid. The mixture was heated to 100° C. for 5 h. The resulting yellow solution was partitioned between 10% aqueous citric acid and ethyl acetate. The organic layer washed with 10% aqueous sodium bicarbonate and brine, dried over magnesium sulfate and evaporated. The residue was purified by chromatography on silica gel with a gradient of heptane to dichloromethane to yield 3.22 g of the title compound as white crystals. MS (ISP) (M+H$^+$)=268.1 and 270.1

Example 1b

5-Amino-6-(4-fluoro-phenyl)-pyrazine-2-carboxylic acid methyl ester

To a solution of 1.87 g 5-bromo-3-(4-fluoro-phenyl)-pyrazin-2-ylamine in 35 ml methanol was added 15 ml ethyl acetate, 0.260 g [1,1'-bis(diphenylphosphino)ferrocen]palladium(II)chloride 1:1 complex with dichloromethane and 1.95 ml triethylamine and the mixture was stirred at 110° C. under 70 bar carbon monoxide for 18 h. The reaction mixture was evaporated and the residue was purified by chromatography on silica gel with heptane:ethyl acetate=1:1 to yield 1.26 g of the title compound as white crystals. MS (ISP) (M+H$^+$)=248.3.

Example 1c

5-Bromo-6-(4-fluoro-phenyl)-pyrazine-2-carboxylic acid methyl ester

To a suspension of 1.26 g 5-amino-6-(4-fluoro-phenyl)-pyrazine-2-carboxylic acid methyl ester in 25.0 ml dibromomethane was added 0.85 ml isoamyl nitrite. To the resulting suspension was added during 30 minutes a solution of 0.82 ml trimethyl bromosilane in 5 ml dibromomethane at room temperature. The mixture was stirred at room temperature for 2 hours. To the resulting turbid solution was added 10% aqueous sodium bicarbonate, the phases were separated and the organic layer was dried over magnesium sulfate, evaporated and purified by chromatography on silica gel using a gradient of heptane to 10% ethyl acetate in heptane to yield 0.81 g of the title compound as white crystals. MS (ISP) (M+H$^+$)=311.1 and 313.0.

Example 1d

5-Bromo-6-(4-fluoro-phenyl)-pyrazine-2-carboxylic acid

To a solution of 0.81 g 5-bromo-6-(4-fluoro-phenyl)-pyrazine-2-carboxylic acid methyl ester in 10 ml tetrahydrofuran was added at room temperature 2.6 ml of a 1M solution of lithium hydroxide in water and the mixture was stirred for 15 minutes. The resulting solution was partitioned between 10% aqueous citric acid and ethyl acetate. The phases were separated and the organic layer washed with water and brine. The organic phase was dried over magnesium sulfate and evaporated to yield 0.78 g of the title compound as white crystals. MS (ISP) (M+H$^+$)=297.2 and 299.0.

Example 1e

5-Bromo-6-(4-fluoro-phenyl)-pyrazine-2-carboxylic acid (2-cyclopropyl-2-hydroxy-propyl)-amide To a solution of 0.78 g of 5-bromo-6-(4-fluoro-phenyl)-pyrazine-2-carboxylic acid in 15.0 ml dichloromethane was added at room temperature 0.39 g (1-chloro-2-methyl-propenyl)-dimethyl-amine and the mixture was stirred for 0.5 hours at room temperature. To the resulting white suspension was added 0.333 g 4-amino-2-cyclopropyl-butan-2-ol and 0.45 ml N-ethyldiisopropylamine and the mixture was stirred for 2 hours at room temperature. The resulting mixture was partitioned between 10% aqueous citric acid and dichloromethane. The phases were separated and the organic layer was dried over magnesium sulfate and evaporated. The residue was purified by chromatography on silica gel using a gradient of heptane to 25% ethyl acetate in heptane to yield 0.70 g of the title compound as white crystals. MS (ISP) (M+H$^+$)=394.1 and 396.0.

Example 2

6-(4-Chloro-phenyl)-5-piperidin-1-yl-pyrazine-2-carboxylic acid (2-cyclopropyl-2-hydroxy-propyl)-amide To a solution of 0.050 g (0.00016 mol) 6-(4-chloro-phenyl)-5-pyrrolidin-1-yl-pyrazine-2-carboxylic acid in 2 ml dimethylformamide was added at room temperature 0.055 g (0.00032 mol) 1,1'-carbonyl-diimidazole and the mixture was stirred at room temperature for 30 min. To the resulting mixture was added 0.072 g (0.00063 mol) 1-amino-2-cyclopropyl-propan-2-ol, and the mixture was stirred at room temperature for 17 hours. The resulting mixture was partitioned between 10% aqueous citric acid and ethyl acetate. The phases were separated and the organic phase was dried over magnesium sulfate and evaporated. The residue was purified by chromatography on silica gel using a gradient of heptane to ethyl acetate to yield 0.043 g (66% yield) of the title compound as slightly yellow oil. MS (ISP) (M+H$^+$)=415.

The starting material 5-bromo-6-(4-chloro-phenyl)-pyrazine-2-carboxylic acid (2-cyclopropyl-2-hydroxy-propyl)-amide was obtained by the following sequence of steps:

Example 2a

5-Bromo-3-(4-chloro-phenyl)-pyrazin-2-ylamine

The title compound was obtained in analogy to example 1a by substituting 4-fluorophenylboronic acid with 4-chlorophenylboronic acid as yellow solid in 78% yield. MS (ISP) (M+H$^+$)=284.0 and 286.0.

Example 2b

5-Bromo-3-(4-chloro-phenyl)-2-piperidin-1-yl-pyrazine

To a solution of 0.5 g (0.0018 mol) 5-bromo-3-(4-chloro-phenyl)-pyrazin-2-ylamine in 10 ml dimethylformamide was added at room temperature 0.240 g sodium hydride 55% in oil (0.006 mol) and 0.49 g 1-bromo-5-chloro-pentane (0.0025 mol) and the mixture was stirred at room temperature for 0.5 hours. Another 0.130 g sodium hydride 55% in oil was added and the mixture was stirred at room temperature for 2.5 h. The resulting mixture was partitioned between 10% aqueous citric acid and ethyl acetate. The phases were separated, the organic phase was dried over magnesium sulfate and evaporated. The residue was purified by chromatography on silica gel using a gradient of 30% ethyl acetate in heptane to ethyl acetate to yield 0.043 g (83% yield) of the title compound as slightly brownish oil. MS (ISP) (M+H$^+$)=354.1 and 356.0.

Example 2c 6-(4-Chloro-phenyl)-5-piperidin-1-yl-pyrazine-2-carboxylic acid methyl ester The title compound was obtained from 5-bromo-3-(4-chloro-phenyl)-2-piperidin-1-yl-pyrazine in analogy to the transformation in example 1b as off-white foam in 85% yield. MS (ISP) (M+H$^+$)=332.2 and 334.2.

Example 2d 6-(4-Chloro-phenyl)-5-piperidin-1-yl-pyrazine-2-carboxylic acid

The title compound was obtained from 6-(4-chloro-phenyl)-5-piperidin-1-yl-pyrazine-2-carboxylic acid methyl ester in analogy to the transformation in example 1d as off-white crystalline solid in 93% yield. MS (ISP) (M+H$^+$)= 318.0 and 320.0. Alternatively the compound of example 2,6-(4-chloro-phenyl)-5-piperidin-1-yl-pyrazine-2-carboxylic acid (2-cyclopropyl-2-hydroxy-propyl)-amide, can be prepared from 5-bromo-6-(4-chloro-phenyl)-pyrazine-2-carboxylic acid (2-cyclopropyl-2-hydroxy-propyl)-amide by the same methodology as in described in example 1.

The starting material, 5-bromo-6-(4-chloro-phenyl)-pyrazine-2-carboxylic acid (2-cyclopropyl-2-hydroxy-propyl)-amide, was prepared by the following sequence of steps.

Example 2e

5-Amino-6-(4-chloro-phenyl)-pyrazine-2-carboxylic acid methyl ester

The title compound was obtained from 5-bromo-3-(4-chloro-phenyl)-pyrazin-2-ylamine (example 2a) in analogy to example 1b as off-white crystalline solid with a melting point at 186-188° C. in 82% yield. MS (ISP) (M+H$^+$)=264.1 and 266.2.

Example 2f

5-Bromo-6-(4-chloro-phenyl)-pyrazine-2-carboxylic acid methyl ester

The title compound was obtained from 5-amino-6-(4-chloro-phenyl)-pyrazine-2-carboxylic acid methyl ester in analogy to example 1c as off-white crystalline solid melting at 104-105° C. in 82% yield.

Example 2g

5-Bromo-6-(4-chloro-phenyl)-pyrazine-2-carboxylic acid

The title compound was obtained from 5-bromo-6-(4-chloro-phenyl)-pyrazine-2-carboxylic acid methyl ester in analogy to example 1d as off-white crystalline solid melting at 190-191° C. in 97.5% yield.

Example 2h

5-Bromo-6-(4-chloro-phenyl)-pyrazine-2-carboxylic acid (2-cyclopropyl-2-hydroxy-propyl)-amide To a suspension of 0.700 g (0.00223 mol) 5-bromo-6-(4-chloro-phenyl)-pyrazine-2-carboxylic acid in 7.0 ml dichloromethane was added a solution of 0.35 g (0.00262 mol) (1-chloro-2-methyl-propenyl)-dimethyl-amine and the mixture was stirred at room temperature for 45 min. To the resulting yellow solution was added dropwise during 15 minutes a solution of 0.296 g (0.00257 mol) 1-amino-2-cyclopropyl-propan-2-ol and 0.433 g ethyldiisopropylamine in 4.0 ml dichloromethane and the mixture was stirred at room temperature for 1 h. The resulting mixture was partitioned between 10% aqueous citric acid and ethyl acetate. The phases were separated and the organic phase was dried over magnesium sulfate and evaporated. The residue was purified by chromatography on silica gel with heptane to ethyl acetate=7:3 to yield 0.748 g (81% Th) of the title compound as slightly yellow foam. MS (ISP) (M+H$^+$)=410.1 and 412.0.

Examples 3 and 4

6-(4-Chloro-phenyl)-5-piperidin-1-yl-pyrazine-2-carboxylic acid ((S)-2-cyclopropyl-2-hydroxy-propyl)-amide and 6-(4-chloro-phenyl)-5-piperidin-1-yl-pyrazine-2-carboxylic acid ((R)-2-cyclopropyl-2-hydroxy-propyl)-amide Racemic 6-(4-chloro-phenyl)-5-piperidin-1-yl-pyrazine-2-carboxylic acid (2-cyclopropyl-2-hydroxy-propyl)-amide (example 2) was separated into the (−) and the (+) enantiomer by chromatography on a Chiral Pack AD column using a mixture of heptane and ethanol as eluent. The compound of example 3 was obtained as white foam MS (ISP) 415.3 (M+H$^+$); 397.0 (M−H$_2$O+H$^+$). The compound of example 4 was obtained as white foam. MS (ISP): 415.3 (M+H$^+$); 397.0 (M−H$_2$O+H$^+$). The stereochemistry was assigned by correlation to examples 3a and 4a.

Examples 3a and 4a

5-Bromo-6-(4-chloro-phenyl)-pyrazine-2-carboxylic acid ((S)-2-cyclopropyl-2-hydroxy-propyl)-amide and 5-bromo-6-(4-chloro-phenyl)-pyrazine-2-carboxylic acid ((R-2-cyclopropyl-2-hydroxy-propyl)-amide Alternatively, the separation of enantiomers can be effected at the stage of 5-bromo-6-(4-chloro-phenyl)-pyrazine-2-carboxylic acid (2-cyclopropyl-2-hydroxy-propyl)-amide (example 2h); again by chromatography on a Chiral Pack AD column using a mixture of heptane and ethanol as eluent. The pure enantiomers were obtained as crystalline solids and the absolute stereochemistry was assigned by X-ray single crystal analysis. The faster eluting (−) enantiomer was determined as 5-bromo-6-(4-chloro-phenyl)-pyrazine-2-carboxylic acid ((S)-2-cyclopropyl-2-hydroxy-propyl)-amide (3a) (m.p.: 127-128° C.) and the slower eluting (+) enantiomer was determined as 5-bromo-6-(4-chloro-phenyl)-pyrazine-2-carboxylic acid ((R-2-cyclopropyl-2-hydroxy-propyl)-amide (4a) (m.p.: 125-126° C.).

Example 5

6-(4-Chloro-phenyl)-5-pyrrolidin-1-yl-pyrazine-2-carboxylic acid ((R)-2-cyclopropyl-2-hydroxy-propyl)-amide To a solution of 0.020 g of 5-bromo-6-(4-chloro-phenyl)-pyrazine-2-carboxylic acid ((R-2-cyclopropyl-2-hydroxy-propyl)-amide (4a) in 2 ml dimethylsulfoxide was added at room temperature 0.017 g of pyrrolidine. The mixture was stirred for 6 hours. The starting material was completely consumed, as evidenced by HPLC and TLC. The reaction mixture was partitioned between 10% citric acid and ethyl acetate. The phases were separated and the organic layer washed with 10% sodium bicarbonate and brine and dried over magnesium sulfate and evaporated. The residue was purified by chromatography on silica gel to yield 0.017 g (89% yield) of the title compound as white foam. MS (ISP) $(M+H^+)=401.3$.

Example 6

5-Azepan-1-yl-6-(4-chloro-phenyl)-pyrazine-2-carboxylic acid ((R)-2-cyclopropyl-2-hydroxy-propyl)-amide In analogy to example 5, however by replacing pyrrolidine with hexamethylene imine, the title compound was obtained as colorless oil (96% yield). MS (ISP) $(M+H^+)=429.5$.

Example 7

6-(4-Chloro-phenyl)-5-[(2-methoxy-ethyl)-methyl-amino]-pyrazine-2-carboxylic acid ((R)-2-cyclopropyl-2-hydroxy-propyl)-amide In analogy to example 5, however by replacing pyrrolidine with N-(2-methoxyethyl)methylamine, the title compound was obtained as oil (46% yield). MS (ISP) $(M+H^+)=419.3$.

Example 8

6-(4-Chloro-phenyl)-5-[methyl-(3-methyl-butyl)-amino]-pyrazine-2-carboxylic acid ((R)-2-cyclopropyl-2-hydroxy-propyl)-amide In analogy to example 5, however by replacing pyrrolidine with methyl isoamylamine, the title compound was obtained as light yellow oil (89% yield). MS (ISP) $(M+H^+)=431.4$.

Example 9

6-(4-Chloro-phenyl)-5-(hexyl-methyl-amino)-pyrazine-2-carboxylic acid ((R)-2-cyclopropyl-2-hydroxy-propyl)-amide In analogy to example 5, however by replacing pyrrolidine with N-methyl hexylamine, the title compound was obtained as light yellow solid (98% yield). MS (ISP) $(M+H^+)=445.3$.

Example 10

6-(4-Chloro-phenyl)-5-(cyclopropylmethyl-amino)-pyrazine-2-carboxylic acid ((R)-2-cyclopropyl-2-hydroxy-propyl)-amide The title compound was obtained as colorless oil (69% yield) in analogy to example 5 by replacing pyrrolidine with aminomethylcyclopropane. MS (ISP) $(M+H^+)=401.3$.

Example 11

5-Azetidin-1-yl-6-(4-chloro-phenyl)-pyrazine-2-carboxylic acid ((R)-2-cyclopropyl-2-hydroxy-propyl)-amide The title compound was obtained as colorless oil (25% yield) in analogy to example 5 by replacing pyrrolidine with azetidine. MS (ISP) $(M+H^+)=387.3$.

Example 12

6-(4-Chloro-phenyl)-5-(3-methoxy-azetidin-1-yl)-pyrazine-2-carboxylic acid ((R)-2-cyclopropyl-2-hydroxy-propyl)-amide In analogy to example 5, however by replacing pyrrolidine with 3-methoxy-azetidine, the title compound was obtained as colorless oil (84% Th). MS (ISP) $(M+H^+)=417.5$.

Example 13

6-(4-Chloro-phenyl)-5-(3-ethoxy-azetidin-1-yl)-pyrazine-2-carboxylic acid ((R)-2-cyclopropyl-2-hydroxy-propyl)-amide The title compound was obtained as colorless oil (93% yield) in analogy to example 5 by replacing pyrrolidine with 3-ethoxy-azetidine. MS (ISP) $(M+H^+)=431.4$.

Example 14

6-(4-Chloro-phenyl)-5-(cyclopropyl-methyl-amino)-pyrazine-2-carboxylic acid ((R)-2-cyclopropyl-2-hydroxy-propyl)-amide In analogy to example 5, however by replacing pyrrolidine with cyclopropyl-methyl-amine, the title compound was obtained as colorless oil (43% yield). MS (ISP) (M+H$^+$)=401.5.

Example 15

6-(4-Chloro-phenyl)-5-(cyclopropylmethyl-methyl-amino)-pyrazine-2-carboxylic acid ((R)-2-cyclopropyl-2-hydroxy-propyl)-amide In analogy to example 5, however by replacing pyrrolidine with cyclopropylmethyl-methyl-amine, the title compound was obtained as colorless oil (43% yield). MS (ISP) (M+H$^+$)=415.5.

Example 16

6-(4-Chloro-phenyl)-5-[(2-hydroxy-ethyl)-methyl-amino]-pyrazine-2-carboxylic acid ((R)-2-cyclopropyl-2-hydroxy-propyl)-amide The title compound was obtained as colorless oil (99% yield) in analogy to example 5 by using 2-(methylamino)ethanol instead of pyrrolidine. MS (ISP) (M+H$^+$)=405.3.

Example 17

6-Phenyl-5-piperidin-1-yl-pyrazine-2-carboxylic acid (2-cyclopropyl-2-hydroxy-propyl)-amide In analogy to example 2, however by starting from 6-phenyl-5-piperidin-1-yl-pyrazine-2-carboxylic acid the title compound was obtained as colorless oil. MS (ISP) (M+H$^+$)=381.5.

The starting material 6-phenyl-5-piperidin-1-yl-pyrazine-2-carboxylic acid was obtained by the following sequence of steps:

Example 17a

5-Bromo-3-phenyl-pyrazin-2-ylamine

In analogy to example 1a, however by replacing 4-fluorophenylboronic acid with phenylboronic acid, the title compound was obtained as yellowish solid (71% yield). MS (ISP) (M+H$^+$)=252.1 and 253.1.

Example 17b

5-Bromo-3-phenyl-2-piperidin-1-yl-pyrazine

In analogy to example 2b, however by starting from 5-bromo-3-phenyl-pyrazin-2-ylamine, the title compound was obtained as yellowish solid (86% yield). MS (ISP) (M+H$^+$)=318.0 and 320.1.

Example 17c

6-Phenyl-5-piperidin-1-yl-pyrazine-2-carboxylic acid methyl ester

In analogy to example 2c, however by starting from 5-bromo-3-phenyl-pyrazin-2-ylamine, the title compound was obtained as yellowish solid (86% yield). MS (ISP) (M+H$^+$)=297.2 and 299.1.

Example 17d

6-Phenyl-5-piperidin-1-yl-pyrazine-2-carboxylic acid

In analogy to example 2d, however by starting from 6-phenyl-5-piperidin-1-yl-pyrazine-2-carboxylic acid methyl ester, the title compound was obtained as slightly yellow solid (95% yield). MS (ISP) (M+H$^+$)=283.1 and 285.1

Example 18

5-[Methyl-(3-methyl-butyl)-amino]-6-(4-trifluoromethyl-phenyl)-pyrazine-2-carboxylic acid ((R)-2-cyclopropyl-2-hydroxy-propyl)-amide By starting from 5-bromo-6-(4-trifluoromethyl-phenyl)-pyrazine-2-carboxylic acid ((R)-2-cyclopropyl-2-hydroxy-propyl)-amide, the title compound was obtained as colorless oil in analogy to example 8. MS (ISP) (M+H$^+$)=465.5.

The starting material, 5-bromo-6-(4-trifluoromethyl-phenyl)-pyrazine-2-carboxylic acid ((R)-2-cyclopropyl-2-hydroxy-propyl)-amide, was obtained by the following sequence of steps:

Example 18a

5-Bromo-3-(4-trifluoromethyl-phenyl)-pyrazin-2-ylamine

In analogy to the procedure as described for example 1a, however by replacing 4-fluorophenylboronic acid with (4-trifluoromethyl)phenylboronic acid, the title compound was obtained as yellowish solid (69% yield). MS (ISP) (M+H$^+$)=317.9 and 320.0.

Example 18b

5-Amino-6-(4-trifluoromethyl-phenyl)-pyrazine-2-carboxylic acid methyl ester

In analogy to example 2e, however by starting from 5-bromo-3-(4-trifluoromethyl-phenyl)-pyrazin-2-ylamine, the title compound was obtained as light brown solid (61% yield). MS (ISP) (M+H$^+$)=298.1.

Example 18c

5-Bromo-6-(4-trifluoromethyl-phenyl)-pyrazine-2-carboxylic acid methyl ester

In analogy to the procedure described for example 2f, the title compound was obtained by starting from 5-amino-6-(4-trifluoromethyl-phenyl)-pyrazine-2-carboxylic acid methyl ester as off white oil (59% yield). MS (ISP) (M+H$^+$)=361.0 and 363.0.

Example 18d

5-Bromo-6-(4-trifluoromethyl-phenyl)-pyrazine-2-carboxylic acid

In analogy to example 2g, the title compound was obtained by starting from 5-bromo-6-(4-trifluoromethyl-phenyl)-pyrazine-2-carboxylic acid methyl ester as off white solid (100% yield). MS (ISP) (M+H$^+$)=346.9 and 348.9.

Example 18e

5-Bromo-6-(4-trifluoromethyl-phenyl)-pyrazine-2-carboxylic acid (2-cyclopropyl-2-hydroxy-propyl)-amide In analogy to example 2h, the title compound was obtained by starting from 5-bromo-6-(4-trifluoromethyl-phenyl)-pyrazine-2-carboxylic acid as white solid (47% yield) MS (ISP) (M+H$^+$)=443.9 and 445.9.

Examples 18f and 18g

5-Bromo-6-(4-trifluoromethyl-phenyl)-pyrazine-2-carboxylic acid ((S)-2-cyclopropyl-2-hydroxy-propyl)-amide and 5-bromo-6-(4-trifluoromethyl-phenyl)-pyrazine-2-carboxylic acid ((R)-2-cyclopropyl-2-hydroxy-propyl)-amide In analogy to the procedure described for the synthesis of examples 3a and 4a, the title compounds were obtained by chiral preparative HPLC of 5-bromo-6-(4-trifluoro-methyl-phenyl)-pyrazine-2-carboxylic acid (2-cyclopropyl-2-hydroxy-propyl)-amide as white foams (43.2% and 43.6% Th). MS (ISP) (M+H$^+$)=444.3 and 446.2; MS (ISP) (M+H$^+$)=444.1 and 446.0.

Example 19

5-(Cyclopropylmethyl-methyl-amino)-6-(4-trifluoromethyl-phenyl)-pyrazine-2-carboxylic acid ((R)-2-cyclopropyl-2-hydroxy-propyl)-amide In analogy to example 15, the title compound was obtained by starting from 5-bromo-6-(4-trifluoromethyl-phenyl)-pyrazine-2-carboxylic acid ((R)-2-cyclopropyl-2-hydroxy-propyl)-amide as light yellow solid. MS (ISP) (M+H$^+$)=449.3.

Example 20

5-(Cyclopropyl-methyl-amino)-6-(4-trifluoromethyl-phenyl)-pyrazine-2-carboxylic acid ((R)-2-cyclopropyl-2-hydroxy-propyl)-amide In analogy to example 14, the title compound was obtained by starting from 5-bromo-6-(4-trifluoromethyl-phenyl)-pyrazine-2-carboxylic acid ((R)-2-cyclopropyl-2-hydroxy-propyl)-amide as light yellow solid. MS (ISP) (M+H$^+$)=435.3.

Example 21

5-(Cyclopropyl-methyl-amino)-6-(4-trifluoromethoxy-phenyl)-pyrazine-2-carboxylic acid ((1R,2R)-2-hydroxy-cyclohexyl)-amide To a solution of 0.052 g of 5-bromo-6-(4-trifluoromethoxy-phenyl)-pyrazine-2-carboxylic acid ((1R,2R)-2-hydroxy-cyclohexyl)-amide in 2 ml dimethylsulfoxide was added at room temperature 0.024 g of cyclopropyl-methyl-amine hydrochloride and 0.04 ml N-ethyldiisopropylamine. The mixture was stirred at room temperature for 72 hours. The reaction mixture was partitioned between 10% aqueous citric acid and ethyl acetate. The phases were separated and the organic layer washed with 10% aqueous sodium bicarbonate and brine, dried over magnesium sulfate and evaporated. The residue was purified by chromatography on silica gel to yield 0.033 g (61% yield) of the title compound as colorless oil. MS (ISP) (M+H$^+$)=451.1.

The starting material 5-bromo-6-(4-trifluoromethoxy-phenyl)-pyrazine-2-carboxylic acid ((1R,2R)-2-hydroxy-cyclohexyl)-amide was prepared by the following sequence of reactions:

Example 21a

5-Bromo-3-(4-trifluoromethoxy-phenyl)-pyrazin-2-ylamine

To a solution of 10.0 g 3,5-dibromo-pyrazin-2-ylamine in 100.0 ml 1,2-dimethoxyethane was added at room temperature 2.285 g of tetrakis(triphenylphosphine) palladium and the mixture was stirred for 0.5 hours. To the resulting orange-red solution was added a solution of 10.5 g sodium carbonate in 50.0 ml water and 8.96 g 4-trifluoro-methoxyphenylboronic acid. The mixture was heated to 100° C. for 6 hours with stirring. The resulting yellow solution was cooled to room temperature and partitioned between 10% aqueous citric acid and ethyl acetate. The organic layer washed with 10% aqueous sodium bicarbonate and brine dried over magnesium sulfate and evaporated. The residue was purified by chromatography on silica gel using a gradient of 100% heptane to 100% ethyl acetate to yield 10.42 g (79% Th) of the title compound as light yellow solid. MS (ISP) (M+H$^+$)=334.1 and 336.4.

Example 21b

5-Amino-6-(4-trifluoromethoxy-phenyl)-pyrazine-2-carboxylic acid methyl ester

To a solution of 10.20 g (0.029 mol) 5-bromo-3-(4-trifluoromethoxy-phenyl)-pyrazin-2-ylamine in 100 ml methanol and 40 ml ethyl acetate was added 0.500 g (0.0006 mol) PdCl$_2$ dppf CH$_2$Cl$_2$ ([1,1'-Bis(diphenylphosphino)ferrocene]palladium(II) chloride dichloromethane adduct, Cas Registry No. [95464-05-4]) and 8.113 ml (5.9 g, 0.058 mol) triethylamine and the mixture was stirred at 110° C. under 70 bar carbon monoxide pressure for 4 h. The solvents were evaporated and the residue was purified by chromatography on silica gel with a gradient of 100% heptane to 100% ethyl acetate to yield 6.800 g (73% yield) of the title compound as off white crystalline solid. MS (ISP) (M+H$^+$)=314.0.

Example 21c

5-Bromo-6-(4-trifluoromethoxy-phenyl)-pyrazine-2-carboxylic acid methyl ester

To a suspension of 6.8 g (0.022 mol) 5-amino-6-(4-trifluoromethoxy-phenyl)-pyrazine-2-carboxylic acid methyl ester in 150 ml dibromomethane was added 3.50 ml (3.052 g; 0.026 mol) isoamylnitrite. To the resulting suspension was added drop wise during 30 minutes a solution of 3.38 ml (3.38 g; 0.026 mol) trimethylbromsilane in 5 ml dibromomethane at 0° C. The mixture was stirred at 0° C. for 0.5 hours and 2 hours at room temperature. To the resulting turbid reaction mixture was added ca 150 ml of a 10% aqueous sodium bicarbonate solution with stirring. The phases were separated the organic phase was dried over magnesium sulfate, evaporated and purified by chromatography on silica gel with a gradient of 100% heptane to 10% ethyl acetate in heptane to yield 6.38 g of the title compound as off white crystalline solid. MS (ISP) (M+H$^+$)=377.0 and 379.0.

Example 21d

5-Bromo-6-(4-trifluoromethoxy-phenyl)-pyrazine-2-carboxylic acid

To a solution of 6.38 g (0.016 mol) 5-bromo-6-(4-trifluoromethoxy-phenyl)-pyrazine-2-carboxylic acid methyl ester in 120 ml tetrahydrofuran was added at room temperature 17 ml of a 1M lithium hydroxide solution in water (0.017 mol) and the mixture was stirred at room temperature for 45 minutes. The resulting clear reaction mixture was partitioned between 10% aqueous citric acid solution and ethyl acetate. The phases were separated and the organic layer washed with water and brine, dried over magnesium sulfate and evaporated to yield 6.05 g (99% yield) of the title compound as white crystalline solid. MS (ISP) (M+H$^+$)=363.0 and 364.9

Example 21e

5-Bromo-6-(4-trifluoromethoxy-phenyl)-pyrazine-2-carboxylic acid ((1R,2R)-2-hydroxy-cyclohexyl)-amide To a solution of 1.0 g (0.0028 mol) of 5-bromo-6-(4-trifluoromethoxy-phenyl)-pyrazine-2-carboxylic acid in 80.0 ml dichloromethane was added at room temperature 0.4 ml (0.405 g 0.0030 mol) (1-chloro-2-methyl-propenyl)-dimethyl-amine and the mixture was stirred for 0.5 hours. To the resulting dark solution was added 0.35 g (0.0030 mol) (1R, 2R)-2-amino-cyclohexanol and 0.94 ml (0.712 g, 0.0060 mol) N-ethyldiisopropylamine and the mixture was stirred at room temperature for 2 hours. The reaction mixture was then partitioned between 10% aqueous citric acid and ethyl acetate. The phases were separated and the organic phase washed with 10% aqueous sodium bicarbonate and brine, dried over magnesium sulfate and evaporated. The residue was purified by chromatography on silica gel with a gradient of 100% heptane to heptane with 40% ethyl acetate to yield 1.107 g of the tile compound as a white waxy solid. MS (ISP) (M+H$^+$)=360.0 and 362.0.

Example 22

5-(Cyclopropylmethyl-methyl-amino)-6-(4-trifluoromethoxy-phenyl)-pyrazine-2-carboxylic acid ((1R, 2R)-2-hydroxy-cyclohexyl)-amide In analogy to example 21, the title compound was obtained by replacing cyclopropyl-methyl-amine hydrochloride with cyclopropylmethyl-methyl-amine hydrochloride as off white foam (22% yield). MS (ISP) (M+H$^+$)=465.4.

Example 23

5-[Methyl-(3-methyl-butyl)-amino]-6-(4-trifluoromethoxy-phenyl)-pyrazine-2-carboxylic acid ((1R, 2R)-2-hydroxy-cyclohexyl)-amide In analogy to example 21, the title compound was obtained by replacing cyclopropyl-methyl-amine hydrochloride with methyl-(3-methyl-butyl)-amine hydrochloride as off white foam (22% yield). MS (ISP) (M+H$^+$)=481.4.

Example 24

5-(Cyclopropyl-methyl-amino)-6-(4-trifluoromethoxy-phenyl)-pyrazine-2-carboxylic acid ((R)-2-cyclopropyl-2-hydroxy-propyl)-amide In analogy to example 14, the title compound was obtained by starting from 5-bromo-6-(4-trifluoromethoxy-phenyl)-pyrazine-2-carboxylic acid ((R)-2-cyclopropyl-2-hydroxy-propyl)-amide as light yellow oil. MS (ISP) (M+H$^+$)=451. The starting material 5-bromo-6-(4-trifluoromethoxy-phenyl)-pyrazine-2-carboxylic acid ((R)-2-cyclopropyl-2-hydroxy-propyl)-amide was obtained from 5-bromo-6-(4-trifluoromethoxy-phenyl)-pyrazine-2-carboxylic acid (example 21d) in analogy to example 2h and example 4a.

Example 25

5-(Cyclopropylmethyl-methyl-amino)-6-(4-trifluoromethoxy-phenyl)-pyrazine-2-carboxylic acid ((R)-2-cyclopropyl-2-hydroxy-propyl)-amide In analogy to example 24, the title compound was obtained as light yellow oil by replacing cyclopropyl-methyl-amine hydrochloride with cyclopropylmethyl-methyl-amine hydrochloride. MS (ISP) (M+H$^+$)=465.

Example 26

6-(4-Chloro-phenyl)-5-(2-methoxy-ethoxy)-pyrazine-2-carboxylic acid ((S)-2-cyclopropyl-2-hydroxy-propyl)-amide To a solution of 0.05 g (0.0006 mol) ethylenglycolmonomethylether in 2 ml dimethylsulfoxide was added at room temperature 0.015 g (0.0004 mol) sodium hydride 55% in oil and the mixture was stirred for 30 minutes at room temperature. To the resulting suspension was added 0.050 g (0.00012 mol) 5-bromo-6-(4-chloro-phenyl)-pyrazine-2-carboxylic acid ((S)-2-cyclopropyl-2-hydroxy-propyl)-amide and the mixture was stirred 2 hours at room temperature. The reaction mixture was then partitioned between 10% aqueous citric acid and ethyl acetate. The phases were separated and the organic layer was washed with 10% aqueous sodium bicarbonate and brine, dried over magnesium sulfate and evapo-

Example 27

6-(4-Chloro-phenyl)-5-(2-methoxy-ethoxy)-pyrazine-2-carboxylic acid ((R)-2-cyclopropyl-2-hydroxy-propyl)-amide In analogy to example 26, the title compound was obtained by starting from 5-bromo-6-(4-chloro-phenyl)-pyrazine-2-carboxylic acid ((R)-2-cyclopropyl-2-hydroxy-propyl)-amide. MS (ISP) (M+H$^+$)=406.4.

Example 28

6-(4-Chloro-phenyl)-5-cyclopentylmethoxy-pyrazine-2-carboxylic acid (2-cyclopropyl-2-hydroxy-propyl)-amide The title compound was prepared in analogy to example 26 starting from 5-bromo-6-(4-chloro-phenyl)-pyrazine-2-carboxylic acid (-2-cyclopropyl-2-hydroxy-propyl)-amide and replacing ethylenglycolmonomethylether by cyclopentylmethanol. MS (ISP) (M+H$^+$)=430.1.

Example 29

6-(4-Chloro-phenyl)-5-cyclopentylmethoxy-pyrazine-2-carboxylic acid ((1R,2R)-2-hydroxy-cyclohexyl)-amide The title compound was prepared in analogy to example 26 starting from 5-bromo-6-(4-chloro-phenyl)-pyrazine-2-carboxylic acid ((1R,2R)-2-hydroxy-cyclohexyl)-amide and replacing ethylenglycolmonomethylether by cyclopentylmethanol. MS (ISP) (M+H$^+$)=430.1.

Example 29a

5-Bromo-6-(4-chloro-phenyl)-pyrazine-2-carboxylic acid ((1R,2R)-2-hydroxy-cyclohexyl)-amide The starting material was prepared in analogy to example 21e by replacing 5-bromo-6-(4-trifluoromethoxy-phenyl)-pyrazine-2-carboxylic acid with 5-bromo-6-(4-chloro-phenyl)-pyrazine-2-carboxylic acid. MS (ISP) (M+H$^+$)=410.0 and 412.0.

Example 30

6-(4-Chloro-phenyl)-5-(2-methoxy-ethoxy)-pyrazine-2-carboxylic acid ((1R,2R)-2-hydroxy-cyclohexyl)-amide The title compound was prepared in analogy to example 26 by using 5-bromo-6-(4-chloro-phenyl)-pyrazine-2-carboxylic acid ((1R,2R)-2-hydroxy-cyclohexyl)-amide instead of 5-bromo-6-(4-chloro-phenyl)-pyrazine-2-carboxylic acid ((S)-2-cyclopropyl-2-hydroxy-propyl)-amide. MS (ISP) (M+H$^+$)=406.1.

Example 31

6-(2,4-Dichloro-phenyl)-5-(2-methoxy-ethoxy)-pyrazine-2-carboxylic acid (2-cyclopropyl-2-hydroxy-propyl)-amide To a solution of 0.030 g (0.0009 mol) of 6-(2,4-dichloro-phenyl)-5-(2-methoxy-ethoxy)-pyrazine-2-carboxylic acid in 2.0 ml dimethylformamide was added at room temperature 0.029 g (0.0018 mol) of 1,1'-carbonyldiimidazole and the mixture was stirred at room temperature for 1 hour. To the resulting brown solution was added 0.020 g (0.0018 mol) 1-amino-2-cyclopropyl-propan-2-ol and the mixture was stirred for 3 hours. The reaction mixture was then partitioned between 10% aqueous citric acid and ethyl acetate. The phases were separated and the organic layer washed with 10% aqueous sodium bicarbonate and brine dried over sodium sulfate and evaporated. The residue was purified by chromatography on silica gel using a gradient of heptane to ethyl acetate to yield 0.021 g of the title compound as colorless oil. MS (ISP) (M+H$^+$)=440.4.

The starting material 6-(2,4-dichloro-phenyl)-5-(2-methoxy-ethoxy)-pyrazine-2-carboxylic acid was prepared by the following sequence of reactions:

Example 31a

5-Bromo-3-(2,4-dichloro-phenyl)-pyrazin-2-ylamine

The title compound was prepared in analogy to example 1a by replacing 4-fluorophenylboronic acid by 2,4-dichlorophenylboronic acid. $^1$H-NMR (CDCl$_3$, δ ppm) 4.53 (s,2H); 7.37-7.43 (m, 2H); 7.54 (d, J=1.5 Hz, 1H); 8.12 (s, 1H).

Example 31b 2,5-Dibromo-3-(2,4-dichloro-phenyl)-pyrazine

The title compound was prepared from 5-bromo-3-(2,4-dichloro-phenyl)-pyrazin-2-ylamine in analogy to the transformation in example 21c and obtained as colorless crystals melting at 128-130° C.

Example 31c

5-Bromo-3-(2,4-dichloro-phenyl)-2-(2-methoxy-ethoxy)-pyrazine

To a solution of 0.077 g (0.001 mol) 2-methoxyethanol in 2 ml dimethylsulfoxide was added at room temperature 0.088 g (0.002 mol) sodium hydride (55% in oil) and the mixture was stirred at room temperature for 1 h. To the resulting solution was added 0.352 g 2,5-dibromo-3-(2,4-dichloro-phenyl)-pyrazine and the mixture was stirred at room temperature for 3 h. The resulting reaction mixture was partitioned between water and ethyl acetate, the phases were separated and the organic phase washed twice with water, dried with sodium sulfate and evaporated. The residue was purified by chromatography on silica gel using dichloromethane:heptane=3:1 to dichloromethane as eluent to yield 0.090 g (24% yield) of the title compound as the faster eluting compound as white crystals melting at 92-93° C. and 0.171 g (45% yield) of its isomer 2-bromo-3-(2,4-dichloro-phenyl)-5-(2-methoxy-ethoxy)-pyrazine as the slower eluting compound as yellowish oil.

Example 31d 3-(2,4-Dichloro-phenyl)-5-(2-methoxy-ethoxy)-pyrazine-2-carboxylic acid methyl ester The title compound was obtained from 5-bromo-3-(2,4-dichloro-phenyl)-2-(2-methoxy-ethoxy)-pyrazine in analogy to the transformation in example 21b. MS (ISP) (M+H$^+$)=357.0 and 359.1.

Example 31e 6-(2,4-Dichloro-phenyl)-5-(2-methoxy-ethoxy)-pyrazine-2-carboxylic acid The title compound was obtained from 3-(2,4-dichloro-phenyl)-5-(2-methoxy-ethoxy)-pyrazine-2-carboxylic acid methyl ester in analogy to the transformation described in example 2d. MS (ISP) (M+H$^+$)=343.1 and 344.9.

Example 32

6-(2,4-Dichloro-phenyl)-5-(2-methoxy-ethoxy)-pyrazine-2-carboxylic acid ((1R,2R)-2-hydroxy-cyclohexyl)-amide In analogy to example 31, the title compound was obtained by replacing 1-amino-2-cyclopropyl-propan-2-ol with (1R,2R)-2-amino-cyclohexanol as light yellow oil (50% yield). MS (ISP) (M+H$^+$)=440.4.

Example 33

6-(4-Chloro-phenyl)-5-(3-methoxy-propoxy)-pyrazine-2-carboxylic acid (2-cyclopropyl-2-hydroxy-propyl)-amide In analogy to example 26, the title compound was obtained by replacing ethylenglycolmonomethylether by propylenglycolmonomethylether. MS (ISP) (M+H$^+$)=420.1.

Example 34

6-(4-Chloro-phenyl)-5-(3-methyl-butoxy)-pyrazine-2-carboxylic acid (2-cyclopropyl-2-hydroxy-propyl)-amide In analogy to example 31, by starting from 6-(4-chloro-phenyl)-5-(3-methyl-butoxy)-pyrazine-2-carboxylic acid the title compound was obtained as colorless oil (47% yield). MS (ISP) (M+H$^+$)=418.3.

The starting material 6-(4-chloro-phenyl)-5-(3-methyl-butoxy)-pyrazine-2-carboxylic acid was obtained by the following sequence of reactions:

Example 34a

5-Bromo-3-(4-chloro-phenyl)-2-(3-methyl-butoxy)-pyrazine

To a suspension of 12.00 g (0.033 mol) 5-bromo-3-(4-chloro-phenyl)-pyrazin-2-ylamine in 80 ml dibromomethane was added 5.93 g isoamyl nitrite. To the resulting mixture was added dropwise during ca 45 min a solution of 7.75 g trimethylbromosilane in 20 ml dibromomethane with stirring at ambient temperature. The mixture was stirred at room temperature for 2 h. To the resulting dark solution was added 100 ml of a 10% aqueous sodium bicarbonate. The phases were separated and the organic phase washed with brine. To the organic phase was added silica gel (ca. 100 g) and the solvent was removed under aspirator vacuum. The product was purified by chromatography with dichloromethane:heptane=1:3 to yield 11.93 g (79% yield) 2,5-dibromo-3-(4-chloro-phenyl)-pyrazine as white crystals melting at 123-125° C. and as a byproduct 0.300 g 5-bromo-3-(4-chloro-phenyl)-2-(3-methyl-butoxy)-pyrazine as a yellow oil. MS (ISP) (M+H$^+$)=357.0 and 355.0.

Example 34b 6-(4-Chloro-phenyl)-5-(3-methyl-butoxy)-pyrazine-2-carboxylic acid methyl ester In analogy to example 1b, the title compound was obtained by starting from 5-bromo-3-(4-chloro-phenyl)-2-(3-methyl-butoxy)-pyrazine in 82% yield as white solid. MS (ISP) (M+H$^+$)=335.2 and 337.2.

Example 34c 6-(4-Chloro-phenyl)-5-(3-methyl-butoxy)-pyrazine-2-carboxylic acid In analogy to example 1c, the title compound was obtained by starting from 6-(4-chloro-phenyl)-5-(3-methyl-butoxy)-pyrazine-2-carboxylic acid methyl ester in quantitative yield as white solid. MS (ISP) (M+H$^+$)=321.1 and 323.2.

Example 35

6-(4-Chloro-phenyl)-5-(3-methyl-butoxy)-pyrazine-2-carboxylic acid ((1R,2R)-2-hydroxy-cyclohexyl)-amide In analogy to example 34, the title compound was obtained as white foam by starting from 6-(4-chloro-phenyl)-5-(3-methyl-butoxy)-pyrazine-2-carboxylic acid and (1R,2R)-2-amino-cyclohexanol. MS (ISP) (M+H$^+$)=418.4.

Example 36

6-(4-Chloro-phenyl)-5-(3-methyl-butoxy)-pyrazine-2-carboxylic acid piperidin-1-ylamide In analogy to example 34, the title compound was obtained as white foam by starting from 6-(4-chloro-phenyl)-5-(3-methyl-butoxy)-pyrazine-2-carboxylic acid and 1-aminopiperidine. MS (ISP) (M+H$^+$)=403.5.

Example 37

6-(4-Chloro-phenyl)-5-(2-methoxy-ethoxy)-pyrazine-2-carboxylic acid (1-hydroxymethyl-cyclopropyl)-amide To a suspension of 0.05 g (0.00016 mol) of 6-(4-chloro-phenyl)-5-(2-methoxy-ethoxy)-pyrazine-2-carboxylic acid in 2.0 ml dichloromethane was added 0.024 g 1-chloro-N,N,2-trimethyl-1-propenylamine and the mixture was stirred at room temperature for 30 min. To the resulting slightly brown solution was added 0.040 g of (1-amino-cyclopropyl)-methanol hydrochloride and dropwise 0.1 ml N-ethyldiisopropylamine. The mixture was stirred at ambient temperature for 30 min. The resulting mixture was partitioned between 10% aqueous citric acid and ethyl acetate. The phases were separated and the organic phase was dried over magnesium sulfate and evaporated. The residue was purified by chromatography on silica gel using a gradient of heptane to ethyl acetate to yield 0.035 g (55% yield) of the title compound as off white solid. MS (ISP) (M+H$^+$)=378.3.

The starting material 6-(4-chloro-phenyl)-5-(2-methoxy-ethoxy)-pyrazine-2-carboxylic acid was obtained by the following sequence of reactions:

Example 37a

5-Bromo-3-(4-chloro-phenyl)-2-(2-methoxy-ethoxy)-pyrazine

To a solution of 2.942 g (0.035 mol) methoxyethanol (dried over molecular sieves 3A) in 50 ml dimethylsulfoxide (dried over molecular sieves 3A) was added 3.37 g sodium hydride 55% in oil (0.077 mol) and the mixture was stirred at room temperature for 30 min. To the resulting solution was added 10.00 g 2,5-dibromo-3-(4-chloro-phenyl)-pyrazine (example 34a) and the mixture was stirred at ambient temperature for 1 h. The dark reaction mixture was partitioned between water and ethyl acetate. The organic phase washed with 10% aqueous citric acid, 10% aqueous sodium bicarbonate and brine, dried over magnesium sulfate and purified by chromatography on silica gel with heptane:dichloromethane=3:1 to yield 2.2 g (18% Th) of the title compound as white crystals melting at 79-80° C.

Example 37b 6-(4-Chloro-phenyl)-5-(2-methoxy-ethoxy)-pyrazine-2-carboxylic acid methyl ester In analogy to example 1b, the title compound was obtained by starting from 5-bromo-3-(4-chloro-phenyl)-2-(2-methoxy-ethoxy)-pyrazine as white solid (82% yield). MS (ISP) (M+H$^+$)=323.3.

Example 37c 6-(4-Chloro-phenyl)-5-(2-methoxy-ethoxy)-pyrazine-2-carboxylic acid In analogy to example 1d, the title compound was obtained by starting from 6-(4-chloro-phenyl)-5-(2-methoxy-ethoxy)-pyrazine-2-carboxylic acid methyl ester as crystalline white solid (83% yield) melting at 155-156° C.

Example 38

6-(4-Chloro-phenyl)-5-(2-methoxy-ethoxy)-pyrazine-2-carboxylic acid piperidin-1-ylamide In analogy to example 36, the title compound was obtained as an off white solid by starting from 6-(4-chloro-phenyl)-5-(2-methoxy-ethoxy)-pyrazine-2-carboxylic acid (54% yield). MS (ISP) (M+H$^+$)=391.1.

Example 39

6-(4-Chloro-phenyl)-5-(2-methoxy-ethoxy)-pyrazine-2-carboxylic acid (1-hydroxy-cyclopropylmethyl)-amide In analogy to example 37, the title compound was obtained as an off white solid by starting from 6-(4-chloro-phenyl)-5-(2-methoxy-ethoxy)-pyrazine-2-carboxylic acid and 1-(aminomethyl)-1-cyclopropanol (33% yield). MS (ISP) (M+H$^+$)=378.3.

Example 40

5-Cyclopropylmethoxy-6-(4-fluoro-phenyl)-pyrazine-2-carboxylic acid (2-cyclopropyl-2-hydroxy-propyl)-amide In analogy to example 26, the title compound was obtained by starting from 5-bromo-6-(4-fluoro-phenyl)-pyrazine-2-carboxylic acid (2-cyclopropyl-2-hydroxy-propyl)-amide and cyclopropylmethanol as white foam (73% yield). MS (ISP) (M+H$^+$)=386.4.

Example 41

6-(4-Fluoro-phenyl)-5-(tetrahydro-furan-2-yl-methoxy)-pyrazine-2-carboxylic acid (2-cyclopropyl-2-hydroxy-propyl)-amide In analogy to example 26, the title compound was obtained as white foam by starting from 5-bromo-6-(4-fluoro-phenyl)-pyrazine-2-carboxylic acid (2-cyclopropyl-2-hydroxy-propyl)-amide and (tetrahydrofuran-2-yl)-methanol (47% yield). MS (ISP) (M+H$^+$)=416.5.

Example 42

6-(4-Chloro-phenyl)-5-[(R)-1-(tetrahydro-furan-2-yl)methoxy]-pyrazine-2-carboxylic acid ((R)-2-cyclopropyl-2-hydroxy-propyl)-amide In analogy to example 26, the title compound was obtained as white foam by starting from 5-bromo-6-(4-chloro-phenyl)-pyrazine-2-carboxylic acid ((R)-2-cyclopropyl-2-hydroxy-propyl)-amide and (R)-1-(tetrahydro-furan-2-yl)-methanol (75% yield). MS (ISP) (M+H$^+$)=432.3.

Example 43

6-(4-Chloro-phenyl)-5-(2-methoxy-ethoxy)-pyrazine-2-carboxylic acid (2,2-dicyclopropyl-2-hydroxy-ethyl)-amide In analogy to example 32, the title compound was obtained as white foam by starting from 6-(4-chloro-phenyl)-5-(2-methoxy-ethoxy)-pyrazine-2-carboxylic acid (example 37c) and 2-amino-1,1-dicyclopropyl-ethanol (36% yield). MS (ISP) (M+H$^+$)=432.3.

The starting material 2-amino-1,1-dicyclopropyl-ethanol was prepared by the following sequence of steps:

Example 43a 1,1-Dicyclopropyl-2-dibenzylamino-ethanol

To 20 ml of a 0.5 M (0.010 mol) solution of cyclopropyl-magnesium chloride in tetrahydrofuran was a solution of 1.00 g (0.004 mol) dibenzylamino-acetic acid ethyl ester in 10 ml tetrahydrofuran and the mixture was allowed to stir at room temperature for 18 h. The reaction mixture was partitioned between 10% aqueous ammonium chloride and ethyl acetate the phases were separated and the organic phase was purified by chromatography on silca gel with heptane:ethyl acetate=9:1 to 4:1 to yield 0.29 g (26% Th) of the title compound as light yellow oil. MS (ISP) (M+H$^+$)=322.3.

Example 43b

2-Amino-1,1-dicyclopropyl-ethanol

To a solution of 0.28 g 1,1-dicyclopropyl-2-dibenzylamino-ethanol (0.00087 mol) in 10 ml methanol was added 0.060 g Pd(OH)$_2$/charcoal (Fluka 7663; 20%) and the mixture was hydrogenated under 8 bar hydrogen pressure at 60° C. for 2 hours. The catalyst was removed by filtration and the mother liquor was concentrated and the residue was purified by chromatography on silicagel with MeCl$_2$/MeOH/NH$_3$ 90:10:1 to yield 0.10 g (81% yield) of the title compound as colorless oil. $^1$H-NMR (CDCl$_3$ 300 MHz, δ ppm) 0.28-0.45 (m, 8H); 0.71-0.78 (m, 2H); 2.77 (s, 2H) ppm.

Example 44

6-(4-Chloro-phenyl)-5-methoxy-pyrazine-2-carboxylic acid (2,2-dicyclopropyl-2-hydroxy-ethyl)-amide In analogy to example 26, the title compound can be obtained as white solid by starting from 5-bromo-6-(4-chloro-phenyl)-pyrazine-2-carboxylic acid (2,2-dicyclopropyl-2-hydroxy-ethyl)-amide and methanol. MS (ISP) (M+H$^+$)=388.3 The starting material 5-bromo-6-(4-chloro-phenyl)-pyrazine-2-carboxylic acid (2,2-dicyclopropyl-2-hydroxy-ethyl)-amide can be prepared from 5-bromo-6-(4-chloro-phenyl)-pyrazine-2-carboxylic acid (example 2g) and 2-amino-1,1-dicyclopropyl-ethanol (example 43b) in analogy to example 2h.

Example 45

6-(4-Chloro-phenyl)-5-(2-methoxy-ethoxy)-pyrazine-2-carboxylic acid (1-hydroxymethyl-cyclopropylmethyl)-amide In analogy to example 37, the title compound was obtained by starting from (1-aminomethyl-cyclopropyl)-methanol and 6-(4-chloro-phenyl)-5-(2-methoxy-ethoxy)-pyrazine-2-carboxylic acid as a crystalline white solid melting at 93-94° C.

Example 46

6-(4-Chloro-phenyl)-5-[(S)-1-(tetrahydro-furan-2-yl) methoxy]-pyrazine-2-carboxylic acid ((R)-2-cyclopropyl-2-hydroxy-propyl)-amide In analogy to example 26, the title compound was obtained by starting from 5-bromo-6-(4-chloro-phenyl)-pyrazine-2-carboxylic acid ((R)-2-cyclopropyl-2-hydroxy-propyl)-amide and (S)-1-(tetrahydro-furan-2-yl)-methanol as white foam (73% yield). MS (ISP) (M+H$^+$)=432.5.

Example 47

6-(4-Chloro-phenyl)-5-(2-hydroxy-ethoxy)-pyrazine-2-carboxylic acid ((R)-2-cyclopropyl-2-hydroxy-propyl)-amide In analogy to example 26, the title compound was obtained by starting from 5-bromo-6-(4-chloro-phenyl)-pyrazine-2-carboxylic acid ((R)-2-cyclopropyl-2-hydroxy-propyl)-amide and ethyleneglycol as white foam (62% yield). MS (ISP) (M+H$^+$)=392.1

Example 48

5-Butoxy-6-(4-chloro-phenyl)-pyrazine-2-carboxylic acid ((R)-2-cyclopropyl-2-hydroxy-propyl)-amide In analogy to example 26, the title compound was obtained as white foam by starting from 5-bromo-6-(4-chloro-phenyl)-pyrazine-2-carboxylic acid ((R)-2-cyclopropyl-2-hydroxy-propyl)-amide and n-butanol (91% yield). MS (ISP) (M+H$^+$)=404.4.

Example 49

6-(4-Chloro-phenyl)-5-(2,2,2-trifluoro-ethoxy)-pyrazine-2-carboxylic acid ((R)-2-cyclopropyl-2-hydroxy-propyl)-amide To a solution of 0.0041 g (0.0001 mol) 5-bromo-6-(4-chloro-phenyl)-pyrazine-2-carboxylic acid ((R)-2-cyclopropyl-2-hydroxy-propyl)-amide in 1.0 ml 2,2,2-trifluoroethanol was added 0.200 g (0.0006 mol) cesium carbonate and the mixture was stirred at room temperature for 7 days. The reaction mixture was partitioned between water and ethyl acetate, the phases were separated and the organic phase was purified by chromatography on silica gel with heptane:ethyl acetate=2:1 to yield 0.042 g (98% yield) of the title compound as white crystals melting at 96-97° C.

Example 50

6-(4-Chloro-phenyl)-5-(2,2,2-trifluoro-1-methyl-ethoxy)-pyrazine-2-carboxylic acid ((R)-2-cyclopropyl-2-hydroxy-propyl)-amide In analogy to example 49, the title compound was obtained as white foam by starting from 5-bromo-6-(4-chloro-phenyl)-pyrazine-2-carboxylic acid ((R)-2-cyclopropyl-2-hydroxy-propyl)-amide and 1,1,1-trifluoro-1-propanol (37% yield). MS (ISP) (M+H$^+$)=444.1.

Example 51

5-Cyclopropylmethoxy-6-(4-fluoro-phenyl)-pyrazine-2-carboxylic acid ((R)-2-cyclopropyl-2-hydroxy-propyl)-amide In analogy to example 26, the title compound was obtained as white foam by starting from 5-bromo-6-(4-fluoro-phenyl)-pyrazine-2-carboxylic acid ((R)-2-cyclopropyl-2-hydroxy-propyl)-amide and cyclopropanol (91% yield). MS (ISP) (M+H$^+$)=386.3.

Example 52

5-Cyclopropylmethoxy-6-(4-fluoro-phenyl)-pyrazine-2-carboxylic acid ((S)-2-cyclopropyl-2-hydroxy-propyl)-amide In analogy to example 26, the title compound was obtained as white foam by starting from 5-bromo-6-(4-fluoro-phenyl)-pyrazine-2-carboxylic acid ((S)-2-cyclopropyl-2-hydroxy-propyl)-amide and cyclopropanol (91% yield). MS (ISP) (M+H$^+$)=386.1.

Example 53

6-(4-Fluoro-phenyl)-5-(2,2,2-trifluoro-ethoxy)-pyrazine-2-carboxylic acid ((R)-2-cyclopropyl-2-hydroxy-propyl)-amide In analogy to example 49, the title compound was obtained by starting from 5-bromo-6-(4-fluoro-phenyl)-pyrazine-2-carboxylic acid ((R)-2-cyclopropyl-2-hydroxy-propyl)-amide as white crystalline solid (100% yield) melting at 103-104° C.

Example 54

6-(4-Fluoro-phenyl)-5-(2,2,2-trifluoro-ethoxy)-pyrazine-2-carboxylic acid ((1R,2R)-2-hydroxy-cyclohexyl)-amide In analogy to example 49, the title compound was obtained by starting from 5-bromo-6-(4-fluoro-phenyl)-pyrazine-2-carboxylic acid ((1R,2R)-2-hydroxy-cyclohexyl)-amide as white crystalline solid (97.5% yield) melting at 133-134° C.

The starting material was obtained as follows:

Example 54a

5-Bromo-6-(4-fluoro-phenyl)-pyrazine-2-carboxylic acid ((1R,2R)-2-hydroxy-cyclohexyl)-amide In analogy to example 21e, the title compound was obtained by starting from 5-bromo-6-(4-fluoro-phenyl)-pyrazine-2-carboxylic acid (example 1d) as white crystalline solid (68% yield). MS (ISP) (M+H$^+$)=394.2 and 396.1.

Example 55

6-(4-Fluoro-phenyl)-5-(2-methoxy-ethoxy)-pyrazine-2-carboxylic acid ((1R,2R)-2-hydroxy-cyclohexyl)-amide In analogy to example 26, the title compound was obtained by starting from 5-bromo-6-(4-fluoro-phenyl)-pyrazine-2-carboxylic acid ((1R,2R)-2-hydroxy-cyclohexyl)-amide as white crystalline solid (78% yield). MS (ISP) (M+H$^+$)=390.4.

Example 56

5-(2-Methoxy-ethoxy)-6-(4-trifluoromethyl-phenyl)-pyrazine-2-carboxylic acid (2-cyclopropyl-2-hydroxy-propyl)-amide In analogy to example 26, the title compound was obtained by starting from 5-bromo-6-(4-trifluoromethyl-phenyl)-pyrazine-2-carboxylic acid (-2-cyclopropyl-2-hydroxy-propyl)-amide (example 18e) as colorless oil (70% yield). MS (ISP) (M+H$^+$)=440.3.

Example 57

5-Cyclopentylmethoxy-6-(4-trifluoromethyl-phenyl)-pyrazine-2-carboxylic acid (2-cyclopropyl-2-hydroxy-propyl)-amide In analogy to example 28, the title compound was obtained by starting from 5-bromo-6-(4-trifluoromethyl-phenyl)-pyrazine-2-carboxylic acid (-2-cyclopropyl-2-hydroxy-propyl)-amide (example 18e) as colorless oil (91% Th). MS (ISP) (M+H$^+$)=464.3.

Example 58

5-(3-Methoxy-propoxy)-6-(4-trifluoromethyl-phenyl)-pyrazine-2-carboxylic acid (2-cyclopropyl-2-hydroxy-propyl)-amide In analogy to example 33, the title compound was obtained by starting from 5-bromo-6-(4-trifluoromethyl-phenyl)-pyrazine-2-carboxylic acid (-2-cyclopropyl-2-hydroxy-propyl)-amide (example 18e) as colorless oil (58% yield). MS (ISP) (M+H$^+$)=436.9.

Example 59

5-[(R)-1-(Tetrahydro-furan-2-yl)methoxy]-6-(4-trifluoromethyl-phenyl)-pyrazine-2-carboxylic acid (2-cyclopropyl-2-hydroxy-propyl)-amide In analogy to example 42, the title compound was obtained by starting from 5-bromo-6-(4-trifluoromethyl-phenyl)-pyrazine-2-carboxylic acid (-2-cyclopropyl-2-hydroxy-propyl)-amide (example 18e) as colorless oil (55% yield). MS (ISP) (M+H$^+$)=466.1.

Example 60

5-(3-Methyl-butoxy)-6-(4-trifluoromethyl-phenyl)-pyrazine-2-carboxylic acid (2-cyclopropyl-2-hydroxy-propyl)-amide The title compound was obtained in analogy to example 56, however by replacing methoxyethanol with 3-methyl butanol as colorless oil (87% yield). MS (ISP) (M+H$^+$)=452.3.

Example 61

5-Butoxy-6-(4-trifluoromethyl-phenyl)-pyrazine-2-carboxylic acid (2-cyclopropyl-2-hydroxy-propyl)-amide The title compound was obtained in analogy to example 56, however by replacing methoxyethanol with n-butanol as colorless oil (72% Th). MS (ISP) (M+H$^+$)=438.1.

Example 62

5-[(S)-1-(Tetrahydro-furan-2-yl)methoxy]-6-(4-trifluoromethyl-phenyl)-pyrazine-2-carboxylic acid ((R)-2-cyclopropyl-2-hydroxy-propyl)-amide The title compound was obtained in analogy to example 46 by starting from 5-bromo-6-(4-trifluoromethyl-phenyl)-pyrazine-2-carboxylic acid ((R)-2-cyclopropyl-2-hydroxy-propyl)-amide (example 18g) the title compound was obtained as colorless oil (23% Th). MS (ISP) (M+H$^+$)=466.3.

Example 63

5-(2,2,2-Trifluoro-ethoxy)-6-(4-trifluoromethyl-phenyl)-pyrazine-2-carboxylic acid ((R)-2-cyclopropyl-2-hydroxy-propyl)-amide In analogy to example 49, the title compound was obtained by starting from 5-bromo-6-(4-trifluoromethyl-phenyl)-pyrazine-2-carboxylic acid ((R)-2-cyclopropyl-2-hydroxy-propyl)-amide (example 18g) as colorless oil (23% yield). MS (ISP) (M+H$^+$)=466.3.

Example 64

5-(2-Methoxy-ethoxy)-6-(4-trifluoromethoxy-phenyl)-pyrazine-2-carboxylic acid ((1R,2R)-2-hydroxy-cyclohexyl)-amide In analogy to example 30, the title compound was obtained by starting from 5-bromo-6-(4-trifluoromethoxy-phenyl)-pyrazine-2-carboxylic acid ((1R,2R)-2-hydroxy-cyclohexyl)-amide (example 21e) as crystalline solid (27% yield). MS (ISP) (M+H$^+$)=456.5.

Example 65

5-Cyclopropylmethoxy-6-(4-trifluoromethoxy-phenyl)-pyrazine-2-carboxylic acid ((1R,2R)-2-hydroxy-cyclohexyl)-amide In analogy to example 64, the title compound was obtained by replacing methoxyethanol with hydroxymethylcyclopropane as crystalline solid (60% yield). MS (ISP) (M+H$^+$)=452.3.

Example 66

5-(2-Methoxy-ethoxy)-6-(4-trifluoromethoxy-phenyl)-pyrazine-2-carboxylic acid ((R)-2-cyclopropyl-2-hydroxy-propyl)-amide In analogy to example 26, the title compound was obtained by starting from 5-bromo-6-(4-trifluoromethoxy-phenyl)-pyrazine-2-carboxylic acid ((R)-2-cyclopropyl-2-hydroxy-propyl)-amide (example 18g) as colorless oil (60% yield). MS (ISP) (M+H$^+$)=455.9.

Example 67

5-Cyclopropylmethoxy-6-(4-trifluoromethoxy-phenyl)-pyrazine-2-carboxylic acid ((R)-2-cyclopropyl-2-hydroxy-propyl)-amide In analogy to example 51, the title compound was obtained as colorless oil by starting from 5-bromo-6-(4-trifluoromethyl-phenyl)-pyrazine-2-carboxylic acid ((R)-2-cyclopropyl-2-hydroxy-propyl)-amide (example 18g) (45% yield). MS (ISP) (M+H$^+$)=452.0.

Example 68

6-(4-Fluoro-phenyl)-5-(pyridin-2-ylmethoxy)-pyrazine-2-carboxylic acid ((R)-2-cyclopropyl-2-hydroxy-propyl)-amide In analogy to example 51, the title compound was obtained as light yellow oil by starting from 5-bromo-6-(4-fluoro-phenyl)-pyrazine-2-carboxylic acid ((R)-2-cyclopropyl-2-hydroxy-propyl)-amide and pyridin-2-yl-methanol. MS (ISP) (M+H$^+$)=423.2.

Example 69

6-(4-Fluoro-phenyl)-5-(pyrimidin-2-ylmethoxy)-pyrazine-2-carboxylic acid ((R)-2-cyclopropyl-2-hydroxy-propyl)-amide In analogy to example 51, the title compound was obtained as light yellow oil by starting from 5-bromo-6-(4-fluoro-phenyl)-pyrazine-2-carboxylic acid ((R)-2-cyclopropyl-2-hydroxy-propyl)-amide and pyrimidin-2-yl-methanol. MS (ISP) (M+H$^+$)=424.2.

Example 70

6-(4-Fluoro-phenyl)-5-(pyridazin-3-ylmethoxy)-pyrazine-2-carboxylic acid ((R)-2-cyclopropyl-2-hydroxy-propyl)-amide In analogy to example 51, the title compound was obtained as light yellow oil by starting from 5-bromo-6-(4-fluoro-phenyl)-pyrazine-2-carboxylic acid ((R)-2-cyclopropyl-2-hydroxy-propyl)-amide and pyridazin-3-yl-methanol. MS (ISP) (M+H$^+$)=424.2.

Example 71

6-(4-Fluoro-phenyl)-5-(pyrimidin-4-ylmethoxy)-pyrazine-2-carboxylic acid ((R)-2-cyclopropyl-2-hydroxy-propyl)-amide In analogy to example 51, the title compound was obtained as light yellow oil by starting from 5-bromo-6-(4-fluoro-phenyl)-pyrazine-2-carboxylic acid ((R)-2-cyclopropyl-2-hydroxy-propyl)-amide and pyrimidin-4-yl-methanol. MS (ISP) (M+H$^+$)=424.2.

Example 72

6-(4-Fluoro-phenyl)-5-(pyrazin-2-ylmethoxy)-pyrazine-2-carboxylic acid ((R)-2-cyclopropyl-2-hydroxy-propyl)-amide In analogy to example 51, the title compound was obtained as light yellow oil by starting from 5-bromo-6-(4-fluoro-phenyl)-pyrazine-2-carboxylic acid ((R)-2-cyclopropyl-2-hydroxy-propyl)-amide and pyrazin-2-yl-methanol. MS (ISP) (M+H$^+$)=424.2.

Example 73

6-(4-Chloro-phenyl)-5-(pyrimidin-2-ylmethoxy)-pyrazine-2-carboxylic acid ((R)-2-cyclopropyl-2-hydroxy-propyl)-amide In analogy to example 26, the title compound was obtained as light yellow solid by starting from 5-bromo-6-(4-chloro-phenyl)-pyrazine-2-carboxylic acid ((R)-2-cyclopropyl-2-hydroxy-propyl)-amide and pyrimidin-2-yl-methanol. MS (ISP) (M+H$^+$)=440.2.

Example 74

5-(Pyrimidin-2-ylmethoxy)-6-(4-trifluoromethoxy-phenyl)-pyrazine-2-carboxylic acid ((R)-2-cyclopropyl-2-hydroxy-propyl)-amide In analogy to example 66, the title compound was obtained as an off-white solid by starting from 5-bromo-6-(4-trifluoromethoxy-phenyl)-pyrazine-2-carboxylic acid ((R)-2-cyclopropyl-2-hydroxy-propyl)-amide (example 18g) and pyrimidin-2-yl-methanol. MS (ISP) (M+H$^+$)=490.2.

Example 75

6-(4-Fluoro-phenyl)-5-(pyridin-2-ylmethoxy)-pyrazine-2-carboxylic acid ((1R,2R)-2-hydroxy-cyclohexyl)-amide In analogy to example 55, the title compound was obtained as an off-white solid by starting from 5-bromo-6-(4-fluoro-phenyl)-pyrazine-2-carboxylic acid ((1R,2R)-2-hydroxy-cyclohexyl)-amide and pyridin-2-yl-methanol. MS (ISP) (M+H$^+$)=423.2.

Example 76

6-(4-Fluoro-phenyl)-5-(pyrimidin-2-ylmethoxy)-pyrazine-2-carboxylic acid ((1R,2R)-2-hydroxy-cyclohexyl)-amide In analogy to example 55, however by starting from 5-bromo-6-(4-fluoro-phenyl)-pyrazine-2-carboxylic acid ((1R,2R)-2-hydroxy-cyclohexyl)-amide and pyrimidin-2-yl-methanol, the title compound was obtained as off-white solid. MS (ISP) (M+H$^+$)=424.2.

Example 77

5-(Pyridin-2-ylmethoxy)-6-(4-trifluoromethoxy-phenyl)-pyrazine-2-carboxylic acid ((1R,2R)-2-hydroxy-cyclohexyl)-amide In analogy to example 64, the title compound was obtained as an off-white solid by starting from 5-bromo-6-(4-trifluoromethoxy-phenyl)-pyrazine-2-carboxylic acid ((1R,2R)-2-hydroxy-cyclohexyl)-amide (example 21e) and pyridin-2-yl-methanol. MS (ISP) (M+H$^+$)=489.2.

Example 78

5-(Pyrimidin-2-ylmethoxy)-6-(4-trifluoromethoxy-phenyl)-pyrazine-2-carboxylic acid ((1R,2R)-2-hydroxy-cyclohexyl)-amide In analogy to example 64, however by starting from 5-bromo-6-(4-trifluoromethoxy-phenyl)-pyrazine-2-carboxylic acid ((1R,2R)-2-hydroxy-cyclohexyl)-amide (example 21e) and pyrimidin-2-yl-methanol the title compound was obtained as an off-white solid. MS (ISP) (M+H$^+$)=490.2.

Example 79

5-(Pyrimidin-4-ylmethoxy)-6-(4-trifluoromethoxy-phenyl)-pyrazine-2-carboxylic acid ((1R,2R)-2-hydroxy-cyclohexyl)-amide In analogy to example 64, the title compound was obtained as light yellow solid by starting from 5-bromo-6-(4-trifluoromethoxy-phenyl)-pyrazine-2-carboxylic acid ((1R,2R)-2-hydroxy-cyclohexyl)-amide (example 21e) and pyrimidin-4-yl-methanol. MS (ISP) (M+H$^+$)=490.2.

Example 80

5-(Pyrazin-2-ylmethoxy)-6-(4-trifluoromethoxy-phenyl)-pyrazine-2-carboxylic acid ((1R,2R)-2-hydroxy-cyclohexyl)-amide In analogy to example 64, the title compound was obtained as brown oil by starting from 5-bromo-6-(4-trifluoromethoxy-phenyl)-pyrazine-2-carboxylic acid ((1R,2R)-2-hydroxy-cyclohexyl)-amide (example 21e) and pyrazin-2-yl-methanol. MS (ISP) (M+H$^+$)=490.2.

Example 81

6-(4-Chloro-phenyl)-5-(pyrimidin-2-ylmethoxy)-pyrazine-2-carboxylic acid ((S)-2-cyclopropyl-2-hydroxy-propyl)-amide In analogy to example 26, however by starting from 5-bromo-6-(4-chloro-phenyl)-pyrazine-2-carboxylic acid ((S)-2-cyclopropyl-2-hydroxy-propyl)-amide and pyrimidin-2-yl-methanol the title compound was obtained as light yellow solid. MS (ISP) (M+H$^+$)=440.2.

GALENICAL EXAMPLES

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. A compound of formula I:

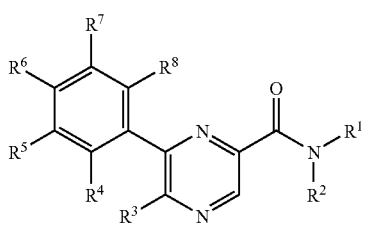

or a pharmaceutically acceptable salt thereof, wherein:
(a) $R^1$ is selected from the group consisting of:
(1) cycloalkyl, which is optionally substituted by a substituent selected from the group consisting of hydroxy, lower alkoxy and lower hydroxyalkyl,
(2) —CH$_2$—(CR$^9$R$^{10}$)$_m$-cycloalkyl, wherein:
(A) $R^9$ is selected from the group consisting of hydrogen, lower alkyl and cycloalkyl;
(B) $R^{10}$ is selected from the group consisting of hydrogen, hydroxy and lower alkoxy;
(C) m is 0 or 1, and
(D) the cycloalkyl is optionally substituted by hydroxy or lower hydroxyalkyl,
(3) piperidinyl, and
(4) —CR$^{11}$R$^{12}$—COOR$^{13}$; wherein:
(A) $R^{11}$ is hydrogen or lower alkyl,
(B) $R^{12}$ is hydrogen or lower alkyl; and
(C) $R^{13}$ is lower alkyl;
(b) $R^2$ is hydrogen;
(c) $R^3$ is —OR$^{14}$, wherein R$^{14}$ is selected from the group consisting of:
(1) lower alkyl,
(2) lower halogenalkyl,
(3) cycloalkyl,
(4) lower cycloalkylalkyl,
(5) lower heterocyclylalkyl,
(6) lower heteroarylalkyl,
(7) lower alkoxyalkyl, and
(8) lower hydroxyalkyl; or
$R^3$ is —NR$^{15}$R$^{16}$ wherein either: (A) $R^{15}$ is hydrogen or lower alkyl, and R$^{16}$ is selected from the group consisting of lower alkyl, cycloalkyl, lower cycloalkylalkyl, lower hydroxyalkyl and lower alkoxyalkyl; or (B) $R^{15}$ and $R^{16}$ together with the nitrogen atom to which they are attached form a heterocyclic ring selected from the group consisting of acetidine, pyrrolidine, piperidine and azepane, wherein said heterocyclic ring is optionally substituted by alkoxy;
(d) $R^4$ is hydrogen or halogen;
(e) $R^5$ is selected from the group consisting of hydrogen, halogen, lower halogenalkyl, lower halogenalkoxy, and cyano;
(f) $R^6$ is selected from the group consisting of hydrogen, halogen, lower halogenalkyl, lower halogenalkoxy, and cyano;
(g) $R^7$ is selected from the group consisting of hydrogen, halogen, lower halogenalkyl, lower halogenalkoxy and cyano; and
(h) $R^8$ is hydrogen or halogen.

2. A compound of formula I according to claim 1, wherein $R^1$ is cycloalkyl which is optionally substituted by a substituent selected from the group consisting of hydroxy, lower alkoxy, and lower hydroxyalkyl.

3. A compound of formula I according to claim 1, wherein $R^1$ is cycloalkyl substituted by hydroxy.

4. A compound of formula I according to claim 1, wherein $R^1$ is —CH$_2$—(CR$^9$R$^{10}$)$_m$-cycloalkyl, wherein: the cycloalkyl is optionally substituted by hydroxy or lower hydroxyalkyl; m is 0 or 1; $R^9$ is selected from the group consisting of hydrogen, lower alkyl and cycloalkyl; and R$^{10}$ is selected from the group consisting of hydrogen, hydroxy and lower alkoxy.

5. A compound of formula I according to claim 1, wherein $R^1$ is —CH$_2$—(CR$^9$R$^{10}$)$_m$-cycloalkyl, wherein: m is 1; $R^9$ is hydrogen or lower alkyl; and $R^{10}$ is hydroxy.

6. A compound of formula I according to claim 1, wherein $R^1$ is —CH$_2$—(CR$^9$R$^{10}$)$_m$-cycloalkyl, wherein: the cycloalkyl is substituted by hydroxy or lower hydroxyalkyl; and m is 0.

7. A compound of formula I according to claim 1, wherein $R^1$ is piperidinyl.

8. A compound of formula I according to claim 1, wherein $R^3$ is —OR$^{14}$, wherein R$^{14}$ is selected from the group consisting of lower alkyl, lower halogenalkyl, cycloalkyl, lower cycloalkylalkyl, lower heterocyclylalkyl, lower heteroarylalkyl, lower alkoxyalkyl, and lower hydroxyalkyl.

9. A compound of formula I according to claim 1, wherein $R^3$ is —$OR^{14}$, wherein $R^{14}$ is lower alkyl or cyloalkyl.

10. A compound of formula I according to claim 1, wherein $R^3$ is —$OR^{14}$, wherein $R^{14}$ is lower alkoxyalkyl or lower hydroxyalkyl.

11. A compound of formula I according to claim 1, wherein $R^3$ is —$OR^{14}$, wherein $R^{14}$ is selected from the group consisting of lower halogen alkyl, lower cycloalkylalkyl, lower heterocyclylalkyl, and lower heteroarylalkyl.

12. A compound of formula I according to claim 1, wherein $R^1$ is —$NR^{15}R^{16}$, wherein: (A) $R^{15}$ is hydrogen or lower alkyl, and $R^{16}$ is selected from the group consisting of lower alkyl, cycloalkyl, lower cycloalkylalkyl, lower hydroxyalkyl and lower alkoxyalkyl; or (B) $R^{15}$ and $R^{16}$ together with the nitrogen atom to which they are attached form a heterocyclic ring selected from the group consisting of acetidine, pyrrolidine, piperidine and azepane, wherein said heterocyclic ring is optionally substituted by alkoxy.

13. A compound of formula I according to claim 1, wherein $R^3$ is —$NR^{15}R^{16}$, wherein: $R^{15}$ is hydrogen or lower alkyl, and $R^{16}$ is selected from the group consisting of lower alkyl, cycloalkyl, lower cycloalkylalkyl, lower hydroxyalkyl and lower alkoxyalkyl.

14. A compound of formula I according to claim 1, wherein $R^3$ is —$NR^{15}R^{16}$, wherein $R^{15}$ and $R^{16}$ together with the nitrogen atom to which they are attached form a heterocyclic ring selected from the group consisting of acetidine, pyrrolidine, piperidine and azepane, wherein said heterocyclic ring is optionally substituted by alkoxy.

15. A compound of formula I according to claim 1, wherein $R^6$ is selected from the group consisting of halogen, lower halogenalkyl, lower halogenalkoxy and cyano.

16. A compound of formula I according to claim 1, wherein $R^4$, $R^5$, $R^7$ and $R^8$ are hydrogen.

17. A compound of formula I according to claim 1, selected from the group consisting of:
   6-(4-chloro-phenyl)-5-[methyl-(3-methyl-butyl)-amino]-pyrazine-2-carboxylic acid ((R)-2-cyclopropyl-2-hydroxy-propyl)-amide,
   6-(4-chloro-phenyl)-5-(cyclopropylmethyl-methyl-amino)-pyrazine-2-carboxylic acid ((R)-2-cyclopropyl-2-hydroxy-propyl)-amide,
   5-(cyclopropylmethyl-methyl-amino)-6-(4-trifluoromethoxy-phenyl)-pyrazine-2-carboxylic acid ((1R,2R)-2-hydroxy-cyclohexyl)-amide,
   5-[methyl-(3-methyl-butyl)-amino]-6-(4-trifluoromethoxy-phenyl)-pyrazine-2-carboxylic acid ((1R,2R)-2-hydroxy-cyclohexyl)-amide,
   5-(cyclopropyl-methyl-amino)-6-(4-trifluoromethoxy-phenyl)-pyrazine-2-carboxylic acid ((R)-2-cyclopropyl-2-hydroxy-propyl)-amide,
   5-(cyclopropylmethyl-methyl-amino)-6-(4-trifluoromethoxy-phenyl)-pyrazine-2-carboxylic acid ((R)-2-cyclopropyl-2-hydroxy-propyl)-amide,
   6-(4-chloro-phenyl)-5-(2-methoxy-ethoxy)-pyrazine-2-carboxylic acid ((R)-2-cyclopropyl-2-hydroxy-propyl)-amide,
   6-(4-chloro-phenyl)-5-(2-methoxy-ethoxy)-pyrazine-2-carboxylic acid ((1R,2R)-2-hydroxy-cyclohexyl)-amide,
   5-cyclopropylmethoxy-6-(4-fluoro-phenyl)-pyrazine-2-carboxylic acid (2-cyclopropyl-2-hydroxy-propyl)-amide,
   6-(4-chloro-phenyl)-5-[(R)-1-(tetrahydro-furan-2-yl)methoxy]-pyrazine-2-carboxylic acid ((R)-2-cyclopropyl-2-hydroxy-propyl)-amide,
   6-(4-chloro-phenyl)-5-[(S)-1-(tetrahydro-furan-2-yl)methoxy]-pyrazine-2-carboxylic acid ((R)-2-cyclopropyl-2-hydroxy-propyl)-amide,
   5-butoxy-6-(4-chloro-phenyl)-pyrazine-2-carboxylic acid ((R)-2-cyclopropyl-2-hydroxy-propyl)-amide,
   6-(4-chloro-phenyl)-5-(2,2,2-trifluoro-ethoxy)-pyrazine-2-carboxylic acid ((R)-2-cyclopropyl-2-hydroxy-propyl)-amide,
   5-cyclopropylmethoxy-6-(4-fluoro-phenyl)-pyrazine-2-carboxylic acid ((R)-2-cyclopropyl-2-hydroxy-propyl)-amide,
   5-(2-methoxy-ethoxy)-6-(4-trifluoromethyl-phenyl)-pyrazine-2-carboxylic acid (2-cyclopropyl-2-hydroxy-propyl)-amide,
   5-(2,2,2-trifluoro-ethoxy)-6-(4-trifluoromethyl-phenyl)-pyrazine-2-carboxylic acid ((R)-2-cyclopropyl-2-hydroxy-propyl)-amide,
   5-(2-methoxy-ethoxy)-6-(4-trifluoromethoxy-phenyl)-pyrazine-2-carboxylic acid ((R)-2-cyclopropyl-2-hydroxy-propyl)-amide
   5-cyclopropylmethoxy-6-(4-trifluoromethoxy-phenyl)-pyrazine-2-carboxylic acid ((R)-2-cyclopropyl-2-hydroxy-propyl)-amide,
   6-(4-fluoro-phenyl)-5-(pyridin-2-ylmethoxy)-pyrazine-2-carboxylic acid ((R)-2-cyclopropyl-2-hydroxy-propyl)-amide,
   6-(4-fluoro-phenyl)-5-(pyrazin-2-ylmethoxy)-pyrazine-2-carboxylic acid ((R)-2-cyclopropyl-2-hydroxy-propyl)-amide,
   6-(4-chloro-phenyl)-5-(pyrimidin-2-ylmethoxy)-pyrazine-2-carboxylic acid ((R)-2-cyclopropyl-2-hydroxy-propyl)-amide, and
any pharmaceutically acceptable salt thereof.

18. A compound of formula I according to claim 1, selected from the group consisting of:
   5-(cyclopropylmethyl-methyl-amino)-6-(4-trifluoromethoxy-phenyl)-pyrazine-2-carboxylic acid ((1R,2R)-2-hydroxy-cyclohexyl)-amide,
   6-(4-chloro-phenyl)-5-(2-methoxy-ethoxy)-pyrazine-2-carboxylic acid ((R)-2-cyclopropyl-2-hydroxy-propyl)-amide,
   6-(4-chloro-phenyl)-5-(2,2,2-trifluoro-ethoxy)-pyrazine-2-carboxylic acid ((R)-2-cyclopropyl-2-hydroxy-propyl)-amide,
   5-cyclopropylmethoxy-6-(4-fluoro-phenyl)-pyrazine-2-carboxylic acid ((R)-2-cyclopropyl-2-hydroxy-propyl)-amide,
   5-cyclopropylmethoxy-6-(4-trifluoromethoxy-phenyl)-pyrazine-2-carboxylic acid ((R)-2-cyclopropyl-2-hydroxy-propyl)-amide, and
any pharmaceutically acceptable salt thereof.

19. A pharmaceutical composition comprising a therapeutically effective amount of a compound of claim 1 and a pharmaceutically acceptable carrier and/or adjuvant.

20. A process for the manufacture of the compounds of formula I as defined in claim 1 comprising:
   (a) coupling a compound of formula

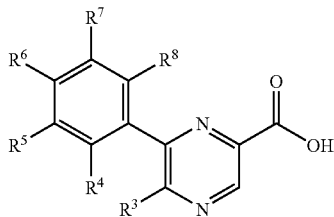

wherein $R^3$ to $R^8$ as defined in claim 1,
with an amine of the formula

H—NR$^1$R$^2$    III wherein $R^1$ and $R^2$ are as defined in claim 1,
in the presence of an activating agent under basic conditions, and (b) optionally converting the resulting compound of formula I into a pharmaceutically acceptable salt thereof.

21. A process for the manufacture of the compounds of formula I as defined in claim 1 comprising:

(a) coupling a compound of formula

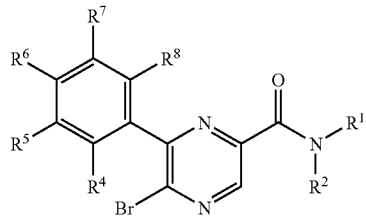

wherein $R^1$, $R^2$ and $R^4$ to $R^8$ are as defined in claim 1,
with an amine of the formula

H—NR$^{15}$R$^{16}$    V wherein R15 and R16 are as defined in claim 1,
in the presence of an activating agent under basic conditions, and (b) optionally converting the resulting compound of formula I into a pharmaceutically acceptable salt thereof.

22. A process for the manufacture of the compounds of formula I as defined in claim 1 comprising:

(a) coupling a compound of formula

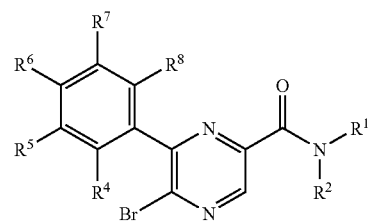

wherein $R^1$, $R^2$ and $R^4$ to $R^8$ are as defined in claim 1,
with an alcohol of the formula

R14—OH    VI wherein $R^{14}$ is as defined in claim 1,
in the presence of a metal hydride or metal carbonate, and (b) optionally converting the resulting compound of formula I into a pharmaceutically acceptable salt thereof.

* * * * *

UNITED STATES PATENT AND TRADEMARK OFFICE
CERTIFICATE OF CORRECTION

PATENT NO. : 7,629,346 B2
APPLICATION NO. : 11/809047
DATED : December 8, 2009
INVENTOR(S) : P. Hebeisen et al.

It is certified that error appears in the above-identified patent and that said Letters Patent is hereby corrected as shown below:

Claim 12, column 53, beginning of line 13, delete "$R^1$" and insert -- $R^3$ --.

Claim 14, column 53, line 27, delete "$NR^{15}R\neq$" and insert -- $NR^{15}R^{16}$ --.

Signed and Sealed this

Sixteenth Day of February, 2010

David J. Kappos
*Director of the United States Patent and Trademark Office*